(12) United States Patent
Jones et al.

(10) Patent No.: US 9,090,646 B2
(45) Date of Patent: Jul. 28, 2015

(54) BIOTINYLATED COMPOUNDS

(71) Applicant: Rutgers, The State University of New Jersey, New Brunswick, NJ (US)

(72) Inventors: Roger A. Jones, New Brunswick, NJ (US); Barbara L. Gaffney, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/096,845

(22) Filed: Dec. 4, 2013

(65) Prior Publication Data

US 2014/0155345 A1 Jun. 5, 2014

Related U.S. Application Data

(60) Provisional application No. 61/733,757, filed on Dec. 5, 2012.

(51) Int. Cl.
*C07H 21/00* (2006.01)
*C07H 19/207* (2006.01)
*C07H 19/10* (2006.01)

(52) U.S. Cl.
CPC .............. *C07H 19/207* (2013.01); *C07H 19/10* (2013.01)

(58) Field of Classification Search
None
See application file for complete search history.

(56) References Cited

U.S. PATENT DOCUMENTS 7,709,458 B2 * 5/2010 Karaolis et al. ................. 514/45
2012/0178710 A1 7/2012 Jones

OTHER PUBLICATIONS

Amiot et al., "New Approach for the Synthesis of c-di-GMP and Its Analogues", Synthesis, 4230-4236 (2006).
Binder et al., "Azide/Alkyne- "Click" Reactions: Applications in Material Science and Organic Synthesis", *Curr. Org. Chem.*, 10, 1791-1815 (2006).
Bock et al., "Cu-Catalyzed Alkyne-Azide "Click" Cycloadditions from a Mechanistic and Synthetic Perspective", *Eur. J. Org. Chem.* 51-68 (2006).
Gaffney et al., "One-flask Syntheses of c-di-GMP and the [$R_p$, $R_p$] and [$R_p$, $S_p$] Thiophosphate Analogs", *Org. Lett.*12 (14), 3269-3271 (2010).
Gaffney et al., "Synthesis of Biotinylated c-di-GMP and c-di-AMP Using Click Conjugation", *Nucleosides Nucleotides Nucleic Acids*32(1), 1-16 (2013).
Galperin et al., "Interplay of heritage and habitat in the distribution of bacterial signal transduction systems", *Mol. BioSyst.*6 (4), 721-728 (2010).
Gomelsky, "cAMP, c-di-GMP, c-di-AMP and now cGMP: bacteria use them all", *Mol. Microbiol.*79 (3), 562-565 (2011).
Grajkowski et al., "Convenient Synthesis of a Propargylated Cyclic (3'-5') Diguanylic Acid and its "Click" Conjugation to a Biotinylated Azide", *Bioconjugate Chem.*21, 2147-2152 (2010).
Moses et al., "The growing applications of click chemistry", *Chem. Soc. Rev.*,36 (8),1249-1262 (2007).
Romling, "Great times for small molecules: c-di-AMP, a second messenger candidate in Bacteria and Archaea", *Sci. Signal*1 (33), pe39 (2008).
Smith et al., "Structural and biochemical determinants of ligand binding by the c-diGMP riboswitch", *Biochemistry*49 (34), 7351-7359 (2010).
Suzuki et al., "Practical Synthesis of Cyclic Bis(3'-5')diadenylic Acid (c-di-AMP)", *Chem. Lett.*40, 1113-1114 (2011).
Zhang et al., "c-di-GMP displays a monovalent metal ion-dependent polymorphism", *J. Am. Chem. Soc.*126 (51), 16700-16701 (2004).
Zhang et al., "Polymorphism of the signaling molecule c-di-GMP",*J. Am. Chem. Soc.*128 (21), 7015-7024 (2006).
Zhao et al., "Thiophosphate analogs of c-di-GMP: impact on polymorphism", *Nucleosides Nucleotides Nucl. Acids*28 (5), 352-378 (2009).

* cited by examiner

*Primary Examiner* — Patrick Lewis
(74) *Attorney, Agent, or Firm* — Viksnins Harris & Padys PLLP

(57) ABSTRACT

The invention provides new biotinylated compounds and methods for their use.

20 Claims, No Drawings

BIOTINYLATED COMPOUNDS

CROSS REFERENCE TO RELATED APPLICATIONS

This patent application claims the benefit of priority of U.S. provisional application Ser. No. 61/733,757, filed Dec. 5, 2012. The content of this provisional application is hereby incorporated herein in its entirety.

STATEMENT OF GOVERNMENT SUPPORT

This invention was made with government support under Grant # GM79760 awarded by the National Institutes of Health. The government has certain rights in the invention.

BACKGROUND

The bacterial signaling molecules cyclic diguanosine monophosphate (c-di-GMP, 6a) and cyclic diadenosine monophosphate (c-di-AMP, 6b) are both key second messengers (Gomelsky, M., cAMP, c-di-GMP, c-di-AMP and now cGMP: Bacteria use them all, *Mol. Microbiol.* 2011, 79, 562-565; Römling, U., Great times for small molecules: c-di-AMP, a second messenger candidate in bacteria and archaea. *Sci. Signal.* 2008, 1, pe39). Because of their critical functions in essential bacterial pathways, c-di-GMP and c-di-AMP have major implications for human health. However, in spite of advances in the identification of proteins and RNA to which c-di-GMP and c-di-AMP bind, a great many additional receptors remain unknown (Galperin, M. Y.; Higdon, R.; Kolker, E., Interplay of heritage and habitat in the distribution of bacterial signal transduction systems. *Mol. BioSyst.* 2010, 6, 721-728). New tools are needed to determine the roles c-di-GMP and c-di-AMP have in human health.

SUMMARY OF CERTAIN EMBODIMENTS OF THE INVENTION

New biotinylated c-di-GMP and c-di-AMP compounds were synthesized. Their availability will allow, e.g., isolation and characterization of new protein and RNA receptors for these key bacterial signaling molecules.

A one-flask, gram-scale synthesis for c-di-GMP and its hydrolysis-resistant [$R_p,R_p$] and [$R_p,S_p$] dithiophosphate analogs was recently reported (Gaffney, B. L.; Veliath, E.; Zhao, J.; Jones, R. A., One-flask syntheses of c-di-GMP and the [Rp,Rp] and [Rp,Sp] thiophosphate analogues. *Org. Lett.* 2010, 12, 3269-3271). In addition, their concentration- and metal-dependent polymorphism have been described, demonstrating that they can associate to form not only self-intercalated dimers, but also higher order guanine quartet assemblies (Zhang, Z.; Gaffney, B. L.; Jones, R. A., c-di-GMP displays a monovalent metal ion-dependent polymorphism. *J. Am. Chem. Soc.* 2004, 126, 16700-16701, Zhang, Z.; Kim, S.; Gaffney, B. L.; Jones, R. A., Polymorphism of the signaling molecule c-di-GMP. *J. Am. Chem. Soc.* 2006, 128, 7015-7024; Zhao, J.; Veliath, E.; Kim, S.; Gaffney, B. L.; Jones, R. A., Thiophosphate analogs of c-di-GMP: impact on polymorphism. *Nucleosides Nucleotides Nucl. Acids* 2009, 28, 352-378).

An approach is presented herein for attaching hexynyl phosphoramidite to the 2'-OH of an intermediate. The resulting alkyne, once fully deprotected, can then be conjugated to a biotinylated azide using click chemistry (Binder, W. H.; Kluger, C., Azide/alkyne-"click" reactions: applications in material science and organic synthesis. *Curr. Org. Chem.* 2006, 10, 1791-1815; Bock, V. D.; Hiemstra, H.; van Maarseveen, J. H.; Cu[1]-catalyzed alkyne-azide "click" cycloadditions from a mechanistic and synthetic perspective. *Eur. J. Org. Chem.* 2006, 51-68; Moses, J. E.; Moorhouse, A. D., The growing applications of click chemistry. *Chem. Soc. Rev.* 2007, 36, 1249-1262) to give 2'-biotinylated c-di-GMP, 10a. The preparation of c-di-AMP, 6b, as well as its biotinylated conjugate, 10b, by the same procedures used for c-di-GMP is also described. The availability of different biotinylated c-di-GMP and c-di-AMP conjugates will prove useful and important for isolation and identification of new receptors.

One embodiment provides as compound of formula I or formula II:

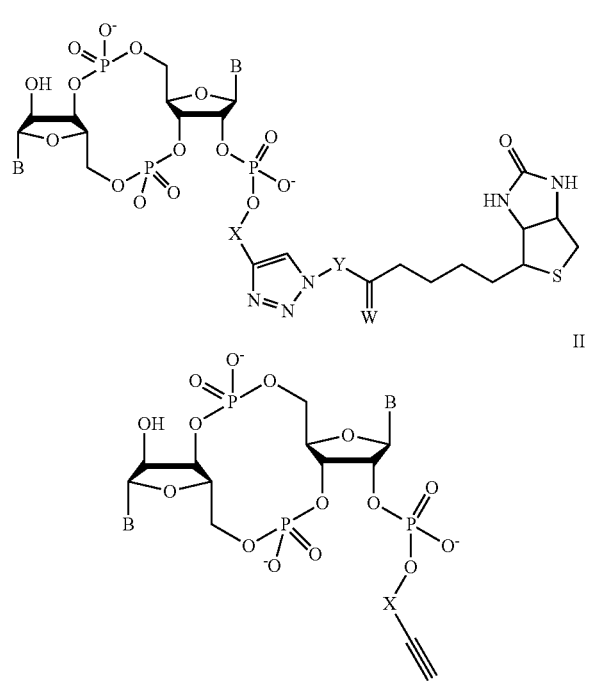

wherein:
each B is independently is

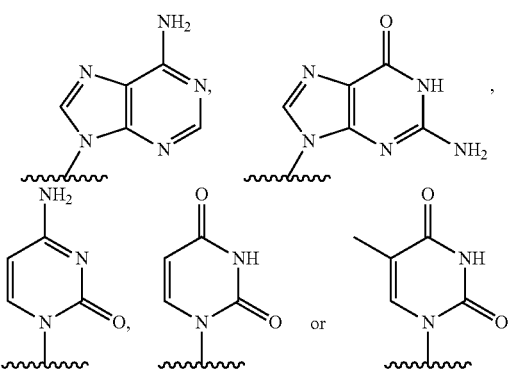

X is $(C_2-C_8)$alkyl, $(C_2-C_8)$alkenyl or $(C_2-C_8)$alkynyl, wherein one or more carbon atoms of the $(C_2-C_8)$alkyl, $(C_2-C_8)$alkenyl or $(C_2-C_8)$alkynyl may be optionally replaced with one or more groups independently selected from O, S, C(=O) and $NR^a$ provided that the O, S or $NR^a$ are not adjacent to any other O, S or NR$^a$, and wherein any (C$_2$-C$_8$)alkyl, (C$_2$-C$_8$)alkenyl or (C$_2$-C$_8$)alkynyl of X is optionally substituted with one or more groups independently selected from halogen, OR$^b$ and NR$^b_2$;

Y is (C$_2$-C$_{28}$)alkyl, (C$_2$-C$_{28}$)alkenyl or (C$_2$-C$_{28}$)alkynyl, wherein one or more carbon atoms of the (C$_2$-C$_{28}$)alkyl, (C$_2$-C$_{28}$)alkenyl or (C$_2$-C$_{28}$)alkynyl may be optionally replaced with one or more groups independently selected from O, S, C(=O) and NR$^c$ provided that the O, S or NR$^c$ are not adjacent to any other O, S or NR$^c$, and wherein any (C$_2$-C$_{28}$)alkyl, (C$_2$-C$_{28}$)alkenyl or (C$_2$-C$_{28}$)alkynyl of Y is optionally substituted with one or more groups independently selected from halogen, OR$^d$ and NR$^d_2$;

W is O or S;

each R$^a$ is independently selected from H and (C$_1$-C$_6$) alkyl;

each R$^b$ is independently selected from H and (C$_1$-C$_6$) alkyl;

each R$^c$ is independently selected from H and (C$_1$-C$_6$) alkyl; and each R$^d$ is independently selected from H and (C$_1$-C$_6$) alkyl;

or a salt thereof.

DETAILED DESCRIPTION

The bacterial signaling molecules cyclic diguanosine monophosphate (c-di-GMP, 6a) and cyclic diadenosine monophosphate (c-di-AMP, 6b) are both key second messengers (Gomelsky, M., 2011; Römling, U., 2008). c-di-GMP has received significant attention as recent research has begun to elucidate its complex, multi-faceted role in facilitating a rapid response to environmental cues by regulating biofilm formation as well as expression of virulence factors (Hengge, R., Principles of c-di-GMP signalling in bacteria. *Nat. Rev. Microbiol.* 2009, 7, 263-273; Krasteva, P. V.; Giglio, K. M.; Sondermann, H., Sensing the messenger: The diverse ways that bacteria signal through c-di-GMP. *Protein Sci.* 2012, 21, 929-948; Mills, E.; Pultz, I. S.; Kulasekara, H. D.; Miller, S. I., The bacterial second messenger c-di-GMP: mechanisms of signalling. *Cell. Microbiol.* 2011, 13, 1122-1129; Povolotsky, T. L.; Hengge, R., 'Life-style' control networks in *Escherichia coli*: Signaling by the second messenger c-di-GMP. *J. Biotechnol.* 2012, 160, 10-16; Quin, M. B.; Berrisford, J. M.; Newman, J. A.; Baslé, A.; Lewis, R. J.; Marles-Wright, J., The bacterial stressosome: A modular system that has been adapted to control secondary messenger signaling. *Structure* 2012, 20, 350-363; Sondermann, H.; Shikuma, N. J.; Yildiz, F. H., You've come a long way: c-di-GMP signaling. *Curr. Opin. Microbiol.* 2012, 15, 140-146). Of several identified protein receptors for c-di-GMP, the best studied is the PilZ domain (Hengge, R., 2009; Krasteva, P. V., 2012, Schirmer, T.; Jenal, U., Structural and mechanistic determinants of c-di-GMP signalling. *Nat Rev Micro* 2009, 7, 724-735) to which it can bind as either a monomer or a self-intercalated dimer (Ko, J.; Ryu, K.-S.; Kim, H.; Shin, J.-S.; Lee, J.-O.; Cheong, C.; Choi, B.-S., Structure of PP4397 reveals the molecular basis for different c-di-GMP binding modes by Pilz domain proteins. *J. Mol. Biol.* 2010, 398, 97-110). In addition, c-di-GMP can bind to two different classes of riboswitch, which are noncoding regulatory mRNA domains (Kulshina, N.; Baird, N. J.; Ferré-D'Amaré, A. R., Recognition of the bacterial second messenger cyclic diguanylate by its cognate riboswitch. *Nat. Struct. Mol. Biol.* 2009, 16, 1212-1217; Lee, E. R.; Baker, J. L.; Weinberg, Z.; Sudarsan, N.; Breaker, R. R., An allosteric self-splicing ribozyme triggered by a bacterial second messenger. *Science (Wash.)* 2010, 329, 845-848, Shanahan, C. A.; Gaffney, B. L.; Jones, R. A.; Strobel, S. A., Differential analog binding by two classes of c-di-GMP riboswitches. *J. Am. Chem. Soc.* 2011, 133, 15578-15592, Smith, K. D.; Lipchock, S. V.; Ames, T. D.; Wang, J.; Breaker, R. R.; Strobel, S. A., Structural basis of ligand binding by a c-di-GMP riboswitch. *Nat. Struct. Mol. Biol.* 2009, 16, 1218-1223, Smith, K. D.; Lipchock, S. V.; Livingston, A. L.; Shanahan, C. A.; Strobel, S. A., Structural and biochemical determinants of ligand binding by the c-di-GMP riboswitch. *Biochemistry* 2010, 49, 7351-7359, Smith, K. D.; Shanahan, C. A.; Moore, E. L.; Simon, A. C.; Strobel, S. A., Structural basis of differential ligand recognition by two classes of bis-(3'-5')-cyclic dimeric guanosine monophosphate-binding riboswitches *Proc. Natl. Acad. Sci. USA* 2011, 108, 7757-7762, Sudarsan, N.; Lee, E. R.; Weinberg, Z.; Moy, R. H.; Kim, J. N.; Link, K. H.; Breaker, R. R., Riboswitches in eubacteria sense the second messenger cyclic di-GMP. *Science (Wash.)* 2008, 321, 411-413). c-di-AMP has only recently been discovered in bacteria, where it serves as a signal to help regulate cell wall synthesis and cell division, including sporulation (Corrigan, R. M.; Abbott, J. C.; Burhenne, H.; Kaever, V.; Gründling, A., c-di-AMP is a new second messenger in *Staphylococcus aureus* with a role in controlling cell size and envelope stress. *PLoS Path.* 2011, 7, e1002217, Luo, Y.; Helmann, J. D., Analysis of the role of *Bacillus subtilis* σ$^M$ in β-lactam resistance reveals an essential role for c-di-AMP in peptidoglycan homeostasis. *Mol. Microbiol.* 2012, 83, 623-639, Oppenheimer-Shaanan, Y.; Wexselblatt, E.; Katzhendler, J.; Yavin, E.; Ben-Yehuda, S., c-di-AMP reports DNA integrity during sporulation in *Bacillus subtilis. EMBO Rep.* 2011, 12, 594-601, Witte, G.; Hartung, S.; Bittner, K.; Hopfner, K.-P., Structural biochemistry of a bacterial checkpoint protein reveals diadenylate cyclase activity regulated by DNA recombination intermediates. *Mol. Cell* 2008, 30, 167-178). In addition, although neither c-di-GMP nor c-di-AMP functions as a second messenger in eukaryotes, they both are known to trigger an innate immune response in infected hosts (Karaolis, D. K. R.; Means, T. K.; Yang, D.; Takahashi, M.; Yoshimura, T.; Muraille, E.; Philpott, D.; Schroeder, J. T.; Hyodo, M.; Hayakawa, Y.; Talbot, B. G.; Brouillette, E.; Malouin, F., Bacterial c-di-GMP is an immunostimulatory molecule. *J. Immunol.* 2007, 178, 2171-2181, Woodward, J. J.; Iavarone, A. T.; Portnoy, D. A., c-di-AMP secreted by intracellular *Listeria monocytogenes* activates a host type I interferon response. *Science* 2010, 328, 1703-1705). A mouse transmembrane protein named STING in the innate immune sensing pathway has recently been identified as a specific receptor for cyclic dinucleotides (Burdette, D. L.; Monroe, K. M.; Sotelo-Troha, K.; Iwig, J. S.; Eckert, B.; Hyodo, M.; Hayakawa, Y.; Vance, R. E., STING is a direct innate immune sensor of cyclic di-GMP. *Nature* 2011, 478, 515-518). Because of their critical functions in essential bacterial pathways, c-di-GMP and c-di-AMP clearly have major implications for human health. However, in spite of advances in the identification of proteins and RNA to which c-di-GMP and c-di-AMP bind, a great many additional receptors remain unknown (Galperin, M. Y.; Higdon, R.; Kolker, E., Interplay of heritage and habitat in the distribution of bacterial signal transduction systems. *Mol. BioSyst.* 2010, 6, 721-728). New tools are needed to determine the roles c-di-GMP and c-di-AMP have in human health.

The term "alkyl" is a straight or branched saturated hydrocarbon. For example, an alkyl group can have 2 to 28 carbon atoms (i.e., (C$_2$-C$_{28}$)alkyl) or 1 to 6 carbon atoms (i.e., (C$_1$-C$_6$) alkyl) or any number of specified carbon atoms.

The term "alkenyl" is a straight or branched hydrocarbon with at least one carbon-carbon double bond. For example, an alkenyl group can have 2 to 28 carbon atoms (i.e., $(C_2\text{-}C_{28})$ alkenyl) or 2 to 6 carbon atoms (i.e., $(C_2\text{-}C_6)$alkenyl) or any number of specified carbon atoms.

The term "alkynyl" is a straight or branched hydrocarbon with at least one carbon-carbon triple bond. For example, an alkynyl group can have 2 to 28 carbon atoms (i.e., $(C_2\text{-}C_{28})$ alkynyl) or 2 to 6 carbon atoms (i.e., $(C_2\text{-}C_6)$alkynyl) or any number of specified carbon atoms.

The term "halo" or "halogen" as used herein refers to fluoro, chloro, bromo and iodo.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities.

When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

In certain embodiments the present invention provides a compound of formula 9a, 9b, 10a, 10b, or a salt thereof

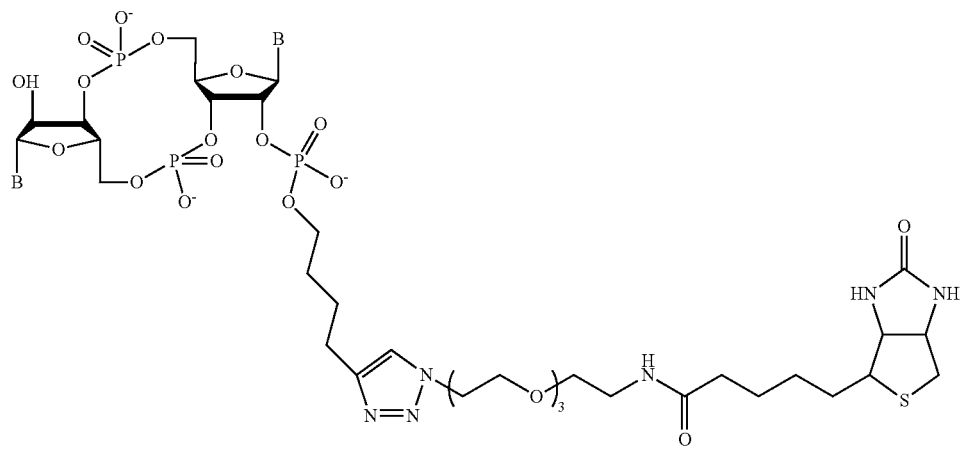

10a: B = G
10b: B = A

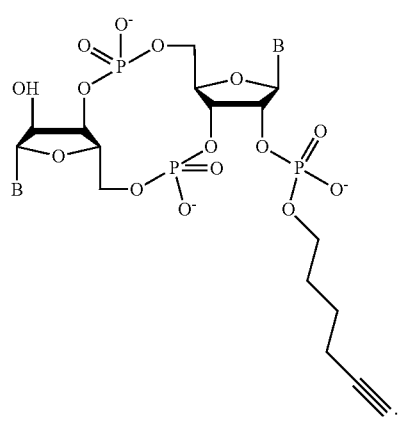

9a: B = G
9b: B = A

In certain embodiments, the invention provides a compound of formula 10a, or a salt thereof.

In certain embodiments, the invention provides a compound of formula 10b, or a salt thereof.

In certain embodiments, the invention provides a compound of formula 9a, or a salt thereof.

In certain embodiments, the invention provides a compound of formula 9b, or a salt thereof.

In certain embodiments, the invention provides a compound of formula 9a or 9b, or a salt thereof, conjugated to a biotinylated azide.

In certain embodiments, the salt is a pharmaceutically acceptable salt.

Certain embodiments of the present invention provide a composition comprising a compound as described herein, or a salt thereof and an acceptable carrier.

In certain embodiments, the compound is not the compound

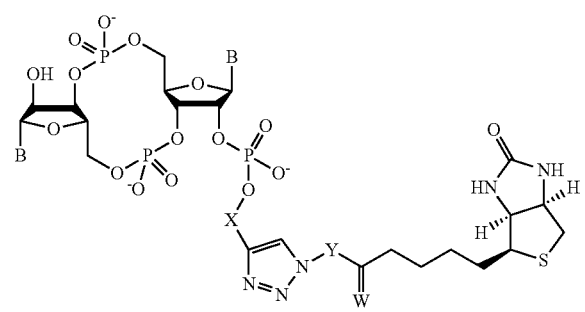

or a salt thereof.

In certain embodiments a biotinylated azide is a compound comprising an azide moiety and biotin (or a derivative of biotin).

Specific values listed below are values for compounds of formulas I, Ia and II. It is to be understood that one or more of the values listed below can be combined with one or more other values.

A specific compound of formula I is a compound of formula Ia:

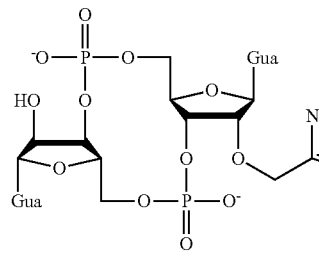

or a salt thereof.

A specific value for each B is:

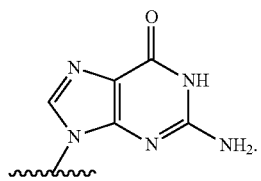 [SMILES: *n1cnc2c(=O)[nH]c(N)nc21]

A specific value for each B is:

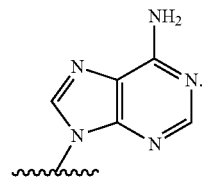

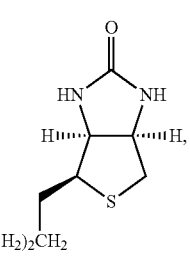

A specific value for W is O.

A specific value for X is $(C_2-C_8)$alkyl, $(C_2-C_8)$alkenyl or $(C_2-C_8)$alkynyl, wherein one or more carbon atoms of the $(C_2-C_8)$alkyl, $(C_2-C_8)$alkenyl or $(C_2-C_8)$alkynyl may be optionally replaced with one or more groups independently selected from O, S, C(=O) and $NR^a$ provided that the O, S or $NR^a$ are not adjacent to any other O, S or $NR^a$, and wherein any $(C_2-C_8)$alkyl, $(C_2-C_8)$alkenyl or $(C_2-C_8)$alkynyl of X is optionally substituted with one or more groups independently selected from halogen, $OR^b$ and $NR^b_2$.

A specific value for X is $(C_3-C_8)$alkyl, $(C_2-C_8)$alkenyl or $(C_2-C_8)$alkynyl, wherein one or more carbon atoms of the $(C_3-C_8)$alkyl, $(C_2-C_8)$alkenyl or $(C_2-C_8)$alkynyl may be optionally replaced with one or more groups independently selected from O, S, C(=O) and $NR^a$ provided that the O, S or $NR^a$ are not adjacent to any other O, S or $NR^a$, and wherein any $(C_3-C_8)$alkyl, $(C_2-C_8)$alkenyl or $(C_2-C_8)$alkynyl of X is optionally substituted with one or more groups independently selected from halogen, $OR^b$ and $NR^b_2$.

A specific value for X is $(C_4-C_8)$alkyl, $(C_2-C_8)$alkenyl or $(C_2-C_8)$alkynyl, wherein one or more carbon atoms of the $(C_4-C_8)$alkyl, $(C_2-C_8)$alkenyl or $(C_2-C_8)$alkynyl may be optionally replaced with one or more groups independently selected from O, S, C(=O) and $NR^a$ provided that the O, S or $NR^a$ are not adjacent to any other O, S or $NR^a$, and wherein any $(C_4-C_8)$alkyl, $(C_2-C_8)$alkenyl or $(C_2-C_8)$alkynyl of X is optionally substituted with one or more groups independently selected from halogen, $OR^b$ and $NR^b_2$.

A specific value for X is $(C_2-C_8)$alkyl, $(C_2-C_8)$alkenyl or $(C_2-C_8)$alkynyl, wherein one or more carbon atoms of the $(C_2-C_8)$alkyl, $(C_2-C_8)$alkenyl or $(C_2-C_8)$alkynyl may be optionally replaced with one or more groups independently selected from O, S, C(=O) and $NR^a$ provided that the O, S or $NR^a$ are not adjacent to any other O, S or $NR^a$.

A specific value for X is $(C_3-C_8)$alkyl, $(C_2-C_8)$alkenyl or $(C_2-C_8)$alkynyl, wherein one or more carbon atoms of the $(C_3-C_8)$alkyl, $(C_2-C_8)$alkenyl or $(C_2-C_8)$alkynyl may be optionally replaced with one or more groups independently selected from O, S, C(=O) and NR$^a$ provided that the O, S or NR$^a$ are not adjacent to any other O, S or NR$^a$.

A specific value for X is (C$_4$-C$_8$)alkyl, (C$_2$-C$_8$)alkenyl or (C$_2$-C$_8$)alkynyl, wherein one or more carbon atoms of the (C$_4$-C$_8$)alkyl, (C$_2$-C$_8$)alkenyl or (C$_2$-C$_8$)alkynyl may be optionally replaced with one or more groups independently selected from O, S, C(=O) and NR$^a$ provided that the O, S or NR$^a$ are not adjacent to any other O, S or NR$^a$.

A specific value for X is (C$_2$-C$_8$)alkyl, (C$_2$-C$_8$)alkenyl or (C$_2$-C$_8$)alkynyl, wherein one or more carbon atoms of the (C$_2$-C$_8$)alkyl, (C$_2$-C$_8$)alkenyl or (C$_2$-C$_8$)alkynyl may be optionally replaced with 1 or 2 groups independently selected from O, S, C(=O) and NR$^a$ provided that the O, S or NR$^a$ are not adjacent to any other O, S or NR$^a$.

A specific value for X is (C$_3$-C$_8$)alkyl, (C$_2$-C$_8$)alkenyl or (C$_2$-C$_8$)alkynyl, wherein one or more carbon atoms of the (C$_3$-C$_8$)alkyl, (C$_2$-C$_8$)alkenyl or (C$_2$-C$_8$)alkynyl may be optionally replaced with 1 or 2 groups independently selected from O, S, C(=O) and NR$^a$ provided that the O, S or NR$^a$ are not adjacent to any other O, S or NR$^a$.

A specific value for X is (C$_4$-C$_8$)alkyl, (C$_2$-C$_8$)alkenyl or (C$_2$-C$_8$)alkynyl, wherein one or more carbon atoms of the (C$_4$-C$_8$)alkyl, (C$_2$-C$_8$)alkenyl or (C$_2$-C$_8$)alkynyl may be optionally replaced with 1 or 2 groups independently selected from O, S, C(=O) and NR$^a$ provided that the O, S or NR$^a$ are not adjacent to any other O, S or NR$^a$.

A specific value for X is (C$_2$-C$_8$)alkyl, wherein one or more carbon atoms of the (C$_2$-C$_8$)alkyl may be optionally replaced with one or more groups independently selected from O, S, C(=O) and NR$^a$ provided that the O, S or NR$^a$ are not adjacent to any other O, S or NR$^a$, and wherein any (C$_2$-C$_8$)alkyl of X is optionally substituted with one or more groups independently selected from halogen, OR$^b$ and NR$^b{}_2$.

A specific value for X is (C$_3$-C$_8$)alkyl, wherein one or more carbon atoms of the (C$_3$-C$_8$)alkyl may be optionally replaced with one or more groups independently selected from O, S, C(=O) and NR$^a$ provided that the O, S or NR$^a$ are not adjacent to any other O, S or NR$^a$, and wherein any (C$_3$-C$_8$)alkyl of X is optionally substituted with one or more groups independently selected from halogen, OR$^b$ and NR$^b{}_2$.

A specific value for X is (C$_4$-C$_8$)alkyl, wherein one or more carbon atoms of the (C$_4$-C$_8$)alkyl may be optionally replaced with one or more groups independently selected from O, S, C(=O) and NR$^a$ provided that the O, S or NR$^a$ are not adjacent to any other O, S or NR$^a$, and wherein any (C$_4$-C$_8$)alkyl of X is optionally substituted with one or more groups independently selected from halogen, OR$^b$ and NR$^b{}_2$.

A specific value for X is (C$_2$-C$_8$)alkyl, wherein one or more carbon atoms of the (C$_2$-C$_8$)alkyl may be optionally replaced with one or more groups independently selected from O, S, C(=O) and NR$^a$ provided that the O, S or NR$^a$ are not adjacent to any other O, S or NR$^a$.

A specific value for X is (C$_3$-C$_8$)alkyl, wherein one or more carbon atoms of the (C$_3$-C$_8$)alkyl may be optionally replaced with one or more groups independently selected from O, S, C(=O) and NR$^a$ provided that the O, S or NR$^a$ are not adjacent to any other O, S or NR$^a$.

A specific value for X is (C$_4$-C$_8$)alkyl, wherein one or more carbon atoms of the (C$_4$-C$_8$)alkyl may be optionally replaced with one or more groups independently selected from O, S, C(=O) and NR$^a$ provided that the O, S or NR$^a$ are not adjacent to any other O, S or NR$^a$.

A specific value for X is (C$_2$-C$_8$)alkyl, wherein one or more carbon atoms of the (C$_2$-C$_8$)alkyl may be optionally replaced with 1 or 2 groups independently selected from O, S, C(=O) and NR$^a$ provided that the O, S or NR$^a$ are not adjacent to any other O, S or NR$^a$.

A specific value for X is (C$_3$-C$_8$)alkyl, wherein one or more carbon atoms of the (C$_3$-C$_8$)alkyl may be optionally replaced with 1 or 2 groups independently selected from O, S, C(=O) and NR$^a$ provided that the O, S or NR$^a$ are not adjacent to any other O, S or NR$^a$.

A specific value for X is (C$_4$-C$_8$)alkyl, wherein one or more carbon atoms of the (C$_4$-C$_8$)alkyl may be optionally replaced with 1 or 2 groups independently selected from O, S, C(=O) and NR$^a$ provided that the O, S or NR$^a$ are not adjacent to any other O, S or NR$^a$.

A specific value for X is (C$_2$-C$_8$)alkyl, (C$_2$-C$_8$)alkenyl or (C$_2$-C$_8$)alkynyl.

A specific value for X is (C$_3$-C$_8$)alkyl, (C$_2$-C$_8$)alkenyl or (C$_2$-C$_8$)alkynyl.

A specific value for X is (C$_4$-C$_8$)alkyl, (C$_2$-C$_8$)alkenyl or (C$_2$-C$_8$)alkynyl.

A specific value for X is (C$_2$-C$_8$)alkyl.

A specific value for X is (C$_3$-C$_8$)alkyl.

A specific value for X is (C$_4$-C$_8$)alkyl.

A specific value for X is (C$_4$-C$_6$)alkyl.

A specific value for X is (C$_4$)alkyl.

A specific value for X is —(CH$_2$)$_4$—.

A specific value for Y is (C$_4$-C$_{28}$)alkyl, (C$_4$-C$_{28}$)alkenyl or (C$_4$-C$_{28}$)alkynyl, wherein one or more carbon atoms of the (C$_4$-C$_{28}$)alkyl, (C$_4$-C$_{28}$)alkenyl or (C$_4$-C$_{28}$)alkynyl may be optionally replaced with one or more groups independently selected from O, S, C(=O) and NR$^c$ provided that the O, S or NR$^c$ are not adjacent to any other O, S or NR$^c$, and wherein any (C$_4$-C$_{28}$)alkyl, (C$_4$-C$_{28}$)alkenyl or (C$_4$-C$_{28}$)alkynyl of Y is optionally substituted with one or more groups independently selected from halogen, OR$^d$ and NR$^d{}_2$.

A specific value for Y is (C$_6$-C$_{28}$)alkyl, (C$_6$-C$_{28}$)alkenyl or (C$_6$-C$_{28}$)alkynyl, wherein one or more carbon atoms of the (C$_6$-C$_{28}$)alkyl, (C$_6$-C$_{28}$)alkenyl or (C$_6$-C$_{28}$)alkynyl may be optionally replaced with one or more groups independently selected from O, S, C(=O) and NR$^c$ provided that the O, S or NR$^c$ are not adjacent to any other O, S or NR$^c$, and wherein any (C$_6$-C$_{28}$)alkyl, (C$_6$-C$_{28}$)alkenyl or (C$_6$-C$_{28}$)alkynyl of Y is optionally substituted with one or more groups independently selected from halogen, OR$^d$ and NR$^d{}_2$.

A specific value for Y is (C$_{10}$-C$_{28}$)alkyl, (C$_{10}$-C$_{28}$)alkenyl or (C$_{10}$-C$_{28}$)alkynyl, wherein one or more carbon atoms of (C$_{10}$-C$_{28}$)alkyl, (C$_{10}$-C$_{28}$)alkenyl or (C$_{10}$-C$_{28}$)alkynyl may be optionally replaced with one or more groups independently selected from O, S, C(=O) and NR$^c$ provided that the O, S or NR$^c$ are not adjacent to any other O, S or NR$^c$, and wherein any (C$_{10}$-C$_{28}$)alkyl, (C$_{10}$-C$_{28}$)alkenyl or (C$_{10}$-C$_{28}$)alkynyl of Y is optionally substituted with one or more groups independently selected from halogen, OR$^d$ and NR$^d{}_2$.

A specific value for Y is (C$_2$-C$_{16}$)alkyl, (C$_2$-C$_{16}$)alkenyl or (C$_2$-C$_{16}$)alkynyl, wherein one or more carbon atoms of the (C$_2$-C$_{16}$)alkyl, (C$_2$-C$_{16}$)alkenyl or (C$_2$-C$_{16}$)alkynyl may be optionally replaced with one or more groups independently selected from O, S, C(=O) and NR$^c$ provided that the O, S or NR$^c$ are not adjacent to any other O, S or NR$^c$, and wherein any (C$_2$-C$_{16}$)alkyl, (C$_2$-C$_{16}$)alkenyl or (C$_2$-C$_{16}$)alkynyl of Y is optionally substituted with one or more groups independently selected from halogen, OR$^d$ and NR$^d{}_2$.

A specific value for Y is (C$_4$-C$_{16}$)alkyl, (C$_4$-C$_{16}$)alkenyl or (C$_4$-C$_{16}$)alkynyl, wherein one or more carbon atoms of the (C$_4$-C$_{16}$)alkyl, (C$_4$-C$_{16}$)alkenyl or (C$_4$-C$_{16}$)alkynyl may be optionally replaced with one or more groups independently selected from O, S, C(=O) and NR$^c$ provided that the O, S or NR$^c$ are not adjacent to any other O, S or NR$^c$, and wherein any (C$_4$-C$_{16}$)alkyl, (C$_4$-C$_{16}$)alkenyl or (C$_4$-C$_{16}$)alkynyl of Y is optionally substituted with one or more groups independently selected from halogen, OR$^d$ and NR$^d{}_2$.

A specific value for Y is $(C_6-C_{16})$alkyl, $(C_6-C_{16})$alkenyl or $(C_6-C_{16})$alkynyl, wherein one or more carbon atoms of is $(C_6-C_{16})$alkyl, $(C_6-C_{16})$alkenyl or $(C_6-C_{16})$alkynyl may be optionally replaced with one or more groups independently selected from O, S, C(=O) or $NR^c$ provided that the O, S or $NR^c$ are not adjacent to any other O, S or $NR^c$, and wherein any is $(C_6-C_{16})$alkyl, $(C_6-C_{16})$alkenyl or $(C_6-C_{16})$alkynyl of Y is optionally substituted with one or more groups independently selected from halogen, $OR^d$ and $NR^d_2$.

A specific value for Y is $(C_{10}-C_{16})$alkyl, $(C_{10}-C_{16})$alkenyl or $(C_{10}-C_{16})$alkynyl, wherein one or more carbon atoms of $(C_{10}-C_{16})$alkyl, $(C_{10}-C_{16})$alkenyl or $(C_{10}-C_{16})$alkynyl may be optionally replaced with one or more groups independently selected from O, S, C(=O) and $NR^c$ provided that the O, S or $NR^c$ are not adjacent to any other O, S or $NR^c$, and wherein any $(C_{10}-C_{16})$alkyl, $(C_{10}-C_{16})$alkenyl or $(C_{10}-C_{16})$alkynyl of Y is optionally substituted with one or more groups independently selected from halogen, $OR^d$ and $NR^d_2$.

A specific value for Y is $(C_4-C_{28})$alkyl, wherein one or more carbon atoms of the $(C_4-C_{28})$alkyl may be optionally replaced with one or more groups independently selected from O, S, C(=O) and $NR^c$ provided that the O, S or $NR^c$ are not adjacent to any other O, S or $NR^c$, and wherein any $(C_4-C_{28})$alkyl of Y is optionally substituted with one or more groups independently selected from halogen, $OR^d$ and $NR^d_2$.

A specific value for Y is $(C_6-C_{28})$alkyl, wherein one or more carbon atoms of the $(C_6-C_{28})$alkyl may be optionally replaced with one or more groups independently selected from O, S, C(=O) and $NR^c$ provided that the O, S or $NR^c$ are not adjacent to any other O, S or $NR^c$, and wherein any $(C_6-C_{28})$alkyl of Y is optionally substituted with one or more groups independently selected from halogen, $OR^d$ and $NR^d_2$.

A specific value for Y is $(C_{10}-C_{28})$alkyl, wherein one or more carbon atoms of $(C_{10}-C_{28})$alkyl may be optionally replaced with one or more groups independently selected from O, S, C(=O) and $NR^c$ provided that the O, S or $NR^c$ are not adjacent to any other O, S or $NR^c$, and wherein any $(C_{10}-C_{28})$alkyl of Y is optionally substituted with one or more groups independently selected from halogen, $OR^d$ and $NR^d_2$.

A specific value for Y is $(C_2-C_{16})$alkyl, wherein one or more carbon atoms of the $(C_2-C_{16})$alkyl may be optionally replaced with one or more groups independently selected from O, S, C(=O) and $NR^c$ provided that the O, S or $NR^c$ are not adjacent to any other O, S or $NR^c$, and wherein any $(C_2-C_{16})$alkyl of Y is optionally substituted with one or more groups independently selected from halogen, $OR^d$ and $NR^d_2$.

A specific value for Y is $(C_4-C_{16})$alkyl, wherein one or more carbon atoms of the $(C_4-C_{16})$alkyl may be optionally replaced with one or more groups independently selected from O, S, C(=O) and $NR^c$ provided that the O, S or $NR^c$ are not adjacent to any other O, S or $NR^c$, and wherein any $(C_4-C_{16})$alkyl of Y is optionally substituted with one or more groups independently selected from halogen, $OR^d$ and $NR^d_2$.

A specific value for Y is $(C_6-C_{16})$alkyl wherein one or more carbon atoms of the $(C_6-C_{16})$alkyl may be optionally replaced with one or more groups independently selected from O, S, C(=O) or $NR^c$ provided that the O, S or $NR^c$ are not adjacent to any other O, S or $NR^c$, and wherein any $(C_6-C_{16})$alkyl of Y is optionally substituted with one or more groups independently selected from halogen, $OR^d$ and $NR^d_2$.

A specific value for Y is $(C_{10}-C_{16})$alkyl, wherein one or more carbon atoms of the $(C_{10}-C_{16})$alkyl may be optionally replaced with one or more groups independently selected from O, S, C(=O) and $NR^c$ provided that the O, S or $NR^c$ are not adjacent to any other O, S or $NR^c$, and wherein any $(C_{10}-C_{16})$alkyl of Y is optionally substituted with one or more groups independently selected from halogen, $OR^d$ and $NR^d_2$.

A specific value for Y is $(C_2-C_{28})$alkyl, $(C_2-C_{28})$alkenyl or $(C_2-C_{28})$alkynyl, wherein one or more carbon atoms of the $(C_2-C_{28})$alkyl, $(C_2-C_{28})$alkenyl or $(C_2-C_{28})$alkynyl may be optionally replaced with one or more groups independently selected from O, S, C(=O) and $NR^c$ provided that the O, S or $NR^c$ are not adjacent to any other O, S or $NR^c$.

A specific value for Y is $(C_4-C_{28})$alkyl, $(C_4-C_{28})$alkenyl or $(C_4-C_{28})$alkynyl, wherein one or more carbon atoms of the $(C_4-C_{28})$alkyl, $(C_4-C_{28})$alkenyl or $(C_4-C_{28})$alkynyl may be optionally replaced with one or more groups independently selected from O, S, C(=O) and $NR^c$ provided that the O, S or $NR^c$ are not adjacent to any other O, S or $NR^c$.

A specific value for Y is $(C_6-C_{28})$alkyl, $(C_6-C_{28})$alkenyl or $(C_6-C_{28})$alkynyl, wherein one or more carbon atoms of the $(C_6-C_{28})$alkyl, $(C_6-C_{28})$alkenyl or $(C_6-C_{28})$alkynyl may be optionally replaced with one or more groups independently selected from O, S, C(=O) and $NR^c$ provided that O, S or $NR^c$ are not adjacent to any other O, S or $NR^c$.

A specific value for Y is $(C_{10}-C_{28})$alkyl, $(C_{10}-C_{28})$alkenyl or $(C_{10}-C_{28})$alkynyl, wherein one or more carbon atoms of $(C_{10}-C_{28})$alkyl, $(C_{10}-C_{28})$alkenyl or $(C_{10}-C_{28})$alkynyl may be optionally replaced with one or more groups independently selected from O, S, C(=O) and $NR^c$ provided that the O, S or $NR^c$ are not adjacent to any other O, S or $NR^c$.

A specific value for Y is $(C_2-C_{16})$alkyl, $(C_2-C_{16})$alkenyl or $(C_2-C_{16})$alkynyl, wherein one or more carbon atoms of the $(C_2-C_{16})$alkyl, $(C_2-C_{16})$alkenyl or $(C_2-C_{16})$alkynyl may be optionally replaced with one or more groups independently selected from O, S, C(=O) and $NR^c$ provided that the O, S or $NR^c$ are not adjacent to any other O, S or $NR^c$.

A specific value for Y is $(C_4-C_{16})$alkyl, $(C_4-C_{16})$alkenyl or $(C_4-C_{16})$alkynyl, wherein one or more carbon atoms of the $(C_4-C_{16})$alkyl, $(C_4-C_{16})$alkenyl or $(C_4-C_{16})$alkynyl may be optionally replaced with one or more groups independently selected from O, S, C(=O) and $NR^c$ provided that the O, S or $NR^c$ are not adjacent to any other O, S or $NR^c$.

A specific value for Y is $(C_6-C_{16})$alkyl, $(C_6-C_{16})$alkenyl or $(C_6-C_{16})$alkynyl, wherein one or more carbon atoms of the $(C_6-C_{16})$alkyl, $(C_6-C_{16})$alkenyl or $(C_6-C_{16})$alkynyl may be optionally replaced with one or more groups independently selected from O, S, C(=O) and $NR^c$ provided that the O, S or $NR^c$ are not adjacent to any other O, S or $NR^c$.

A specific value for Y is $(C_{10}-C_{16})$alkyl, $(C_{10}-C_{16})$alkenyl or $(C_{10}-C_{16})$alkynyl, wherein one or more carbon atoms of the $(C_{10}-C_{16})$alkyl, $(C_{10}-C_{16})$alkenyl or $(C_{10}-C_{16})$alkynyl may be optionally replaced with one or more groups independently selected from O, S, C(=O) and $NR^c$ provided that the O, S or $NR^c$ are not adjacent to any other O, S or $NR^c$.

A specific value for Y is $(C_2-C_{28})$alkyl, wherein one or more carbon atoms of the $(C_2-C_{28})$alkyl may be optionally replaced with one or more groups independently selected from O, C(=O) and $NR^c$ provided that the O or $NR^c$ are not adjacent to any other O or $NR^c$.

A specific value for Y is $(C_4-C_{28})$alkyl, wherein one or more carbon atoms of the $(C_4-C_{28})$alkyl may be optionally replaced with one or more groups independently selected from O, C(=O) and $NR^c$ provided that the O or $NR^c$ are not adjacent to any other O or $NR^c$.

A specific value for Y is $(C_6-C_{28})$alkyl, wherein one or more carbon atoms of the $(C_6-C_{28})$alkyl may be optionally replaced with one or more groups independently selected from O, C(=O) and Me provided that the O or $NR^c$ are not adjacent to any other O or $NR^c$.

A specific value for Y is $(C_{10}-C_{28})$alkyl, wherein one or more carbon atoms of the $(C_{10}-C_{28})$alkyl may be optionally replaced with one or more groups independently selected from O, C(=O) and $NR^c$ provided that the O or $NR^c$ are not adjacent to any other O or $NR^c$.

A specific value for Y is $(C_2-C_{16})$alkyl, wherein one or more carbon atoms of the $(C_2-C_{16})$alkyl may be optionally replaced with one or more groups independently selected from O, C(=O) and $NR^c$ provided that the O or $NR^c$ are not adjacent to any other O or $NR^c$.

A specific value for Y is $(C_4-C_{16})$alkyl, wherein one or more carbon atoms of the $(C_4-C_{16})$alkyl may be optionally replaced with one or more groups independently selected from O, C(=O) and $NR^c$ provided that the O or $NR^c$ are not adjacent to any other O or $NR^c$.

A specific value for Y is $(C_6-C_{16})$alkyl, wherein one or more carbon atoms of the $(C_6-C_{16})$alkyl may be optionally replaced with one or more groups independently selected from O, C(=O) and $NR^c$ provided that the O or $NR^c$ are not adjacent to any other O or $NR^c$.

A specific value for Y is $(C_{10}-C_{16})$alkyl, wherein one or more carbon atoms of the $(C_{10}-C_{16})$alkyl may be optionally replaced with one or more groups independently selected from O, C(=O) and $NR^c$ provided that the O or $NR^c$ are not adjacent to any other O or $NR^c$.

A specific value for Y is $(C_2-C_{28})$alkyl, wherein one or more carbon atoms of the $(C_2-C_{28})$alkyl may be optionally replaced with 1-5 groups independently selected from O and $NR^c$ provided that the O or $NR^c$ are not adjacent to any other O or $NR^c$.

A specific value for Y is $(C_4-C_{28})$alkyl, wherein one or more carbon atoms of the $(C_4-C_{28})$alkyl may be optionally replaced with 1-5 groups independently selected from O and $NR^c$ provided that the O or $NR^c$ are not adjacent to any other O or $NR^c$.

A specific value for Y is $(C_6-C_{28})$alkyl, wherein one or more carbon atoms of the $(C_6-C_{28})$alkyl may be optionally replaced with 1-5 groups independently selected from O and $NR^c$ provided that the O or $NR^c$ are not adjacent to any other O or $NR^c$.

A specific value for Y is $(C_{10}-C_{28})$alkyl, wherein one or more carbon atoms of $(C_{10}-C_{28})$alkyl may be optionally replaced with 1-5 groups independently selected from O and $NR^c$ provided that the O or $NR^c$ are not adjacent to any other O or $NR^c$.

A specific value for Y is $(C_2-C_{16})$alkyl, wherein one or more carbon atoms of the $(C_2-C_{16})$alkyl may be optionally replaced with 1-5 groups independently selected from O and $NR^c$ provided that the O or $NR^c$ are not adjacent to any other O or $NR^c$.

A specific value for Y is $(C_4-C_{16})$alkyl, wherein one or more carbon atoms of the $(C_4-C_{16})$alkyl may be optionally replaced with 1-5 groups independently selected from O and $NR^c$ provided that the O or $NR^c$ are not adjacent to any other O or $NR^c$.

A specific value for Y is $(C_6-C_{16})$alkyl, wherein one or more carbon atoms of the $(C_6-C_{16})$alkyl may be optionally replaced with 1-5 groups independently selected from O and $NR^c$ provided that the O or $NR^c$ are not adjacent to any other O or $NR^c$.

A specific value for Y is $(C_{10}-C_{16})$alkyl, wherein one or more carbon atoms of the $(C_{10}-C_{16})$alkyl may be optionally replaced with 1-5 groups independently selected from O and $NR^c$ provided that the O or $NR^c$ are not adjacent to any other O or $NR^c$.

A specific value for Y is $(C_{10}-C_{14})$alkyl, wherein one or more carbon atoms of the $(C_{10}-C_{14})$alkyl may be optionally replaced with 1-5 groups independently selected from O and $NR^c$ provided that the O or $NR^c$ are not adjacent to any other O or $NR^c$.

A specific value for Y is:

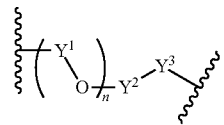

wherein n is 0, 1, 2, 3 or 4;
each $Y^1$ is independently $(C_2-C_4)$alkyl;
$Y^2$ is $(C_2-C_6)$alkyl;
$Y^3$ is —$NR^{Y4}$—, —O— or —S—; and
$R^{Y4}$ is H or $(C_1-C_6)$alkyl.

A specific value for Y is:

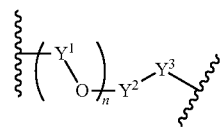

wherein n is 0, 1, 2, 3, 4 or 5;
each $Y^1$ is independently $(C_2-C_3)$alkyl;
$Y^2$ is $(C_2-C_6)$alkyl;
$Y^3$ is —$NR^{Y4}$—; and
$Y^4$ is H or $(C_1-C_6)$alkyl.

A specific value for Y is:

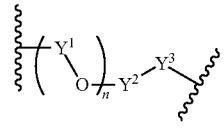

wherein n is 1, 2, 3 or 4;
each $Y^1$ is independently $(C_2-C_4)$alkyl;
$Y^2$ is $(C_2-C_4)$alkyl;
$Y^3$ is —$NR^{Y4}$—; and
$Y^4$ is H or $(C_1-C_6)$alkyl A specific value for Y is:

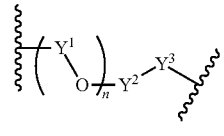

wherein n is 1, 2, 3 or 4;
$Y^1$ is $(C_2)$alkyl;
$Y^2$ is $(C_2-C_4)$alkyl;
$Y^3$ is —NH—.

A specific value for Y is:

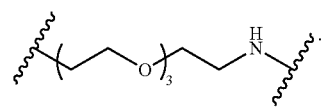

A specific group of compound of formula I are compounds wherein each $R^a$, $R^b$, $R^c$ and $R^d$ is H.

A specific compound of formula I is:
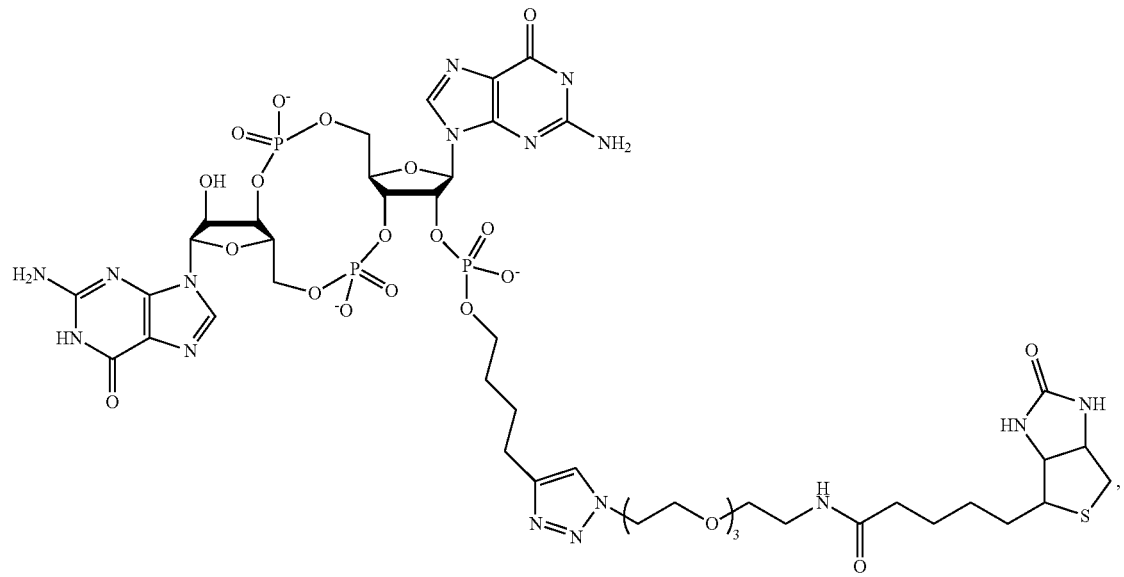
10a
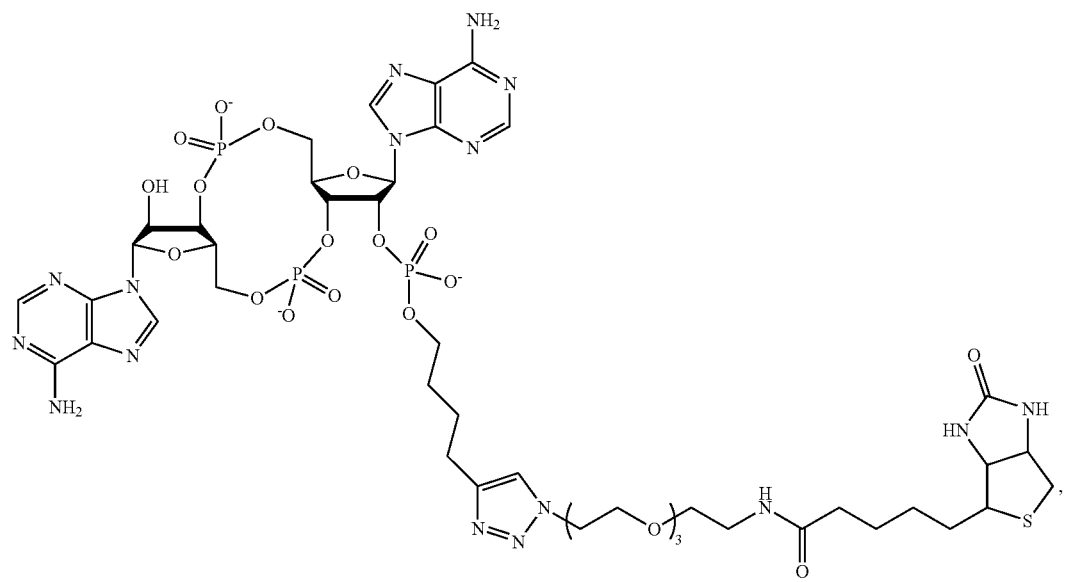
10b
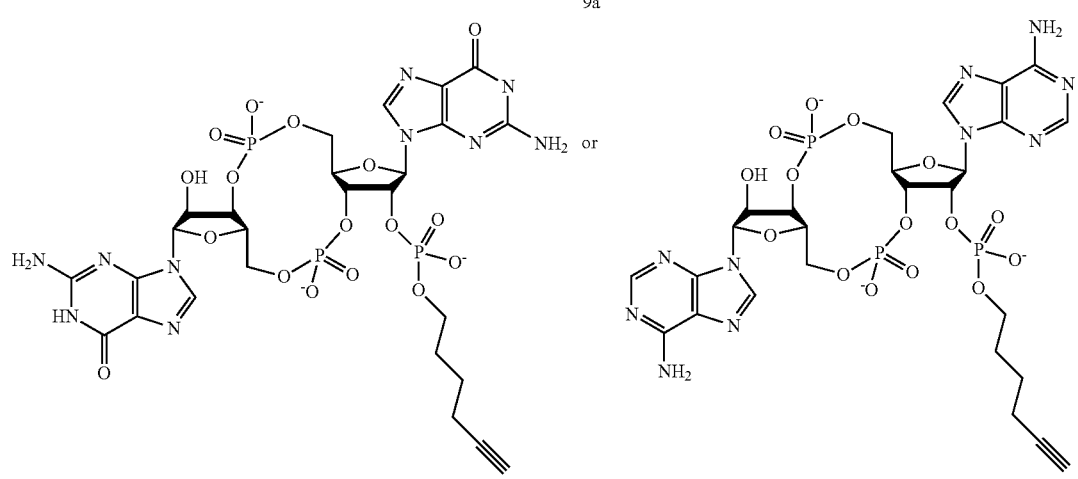
9a            9b
or a salt thereof.

One embodiment provides as compound of formula I' or formula II':

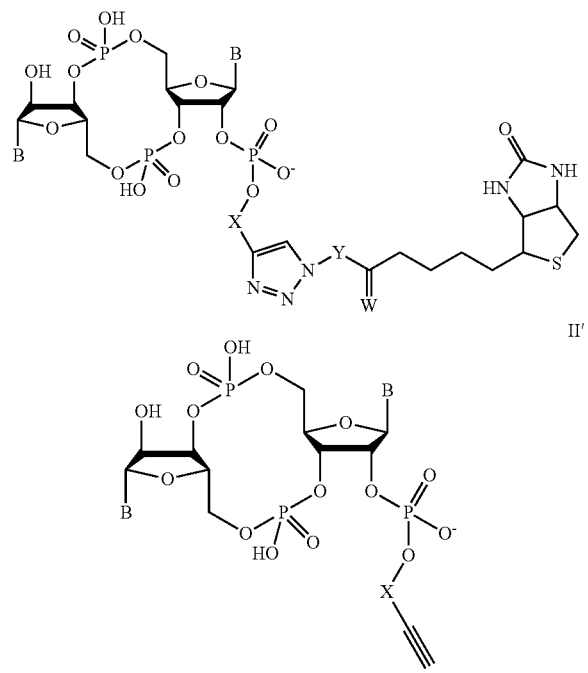

wherein:
each B is independently is

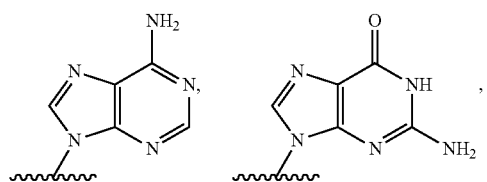

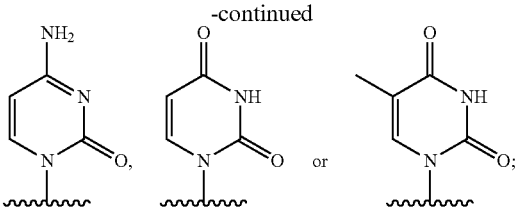

X is $(C_2-C_8)$alkyl, $(C_2-C_8)$alkenyl or $(C_2-C_8)$alkynyl, wherein one or more carbon atoms of the $(C_2-C_8)$alkyl, $(C_2-C_8)$alkenyl or $(C_2-C_8)$alkynyl may be optionally replaced with one or more groups independently selected from O, S, C(=O) and $NR^a$ provided that the O, S or $NR^a$ are not adjacent to any other O, S or $NR^a$, and wherein any $(C_2-C_8)$alkyl, $(C_2-C_8)$alkenyl or $(C_2-C_8)$alkynyl of X is optionally substituted with one or more groups independently selected from halogen, $OR^b$ and $NR^b{}_2$;

Y is $(C_2-C_{28})$alkyl, $(C_2-C_{28})$alkenyl or $(C_2-C_{28})$alkynyl, wherein one or more carbon atoms of the $(C_2-C_{28})$alkyl, $(C_2-C_{28})$alkenyl or $(C_2-C_{28})$alkynyl may be optionally replaced with one or more groups independently selected from O, S, C(=O) and $NR^c$ provided that the O, S or $NR^c$ are not adjacent to any other O, S or $NR^c$, and wherein any $(C_2-C_{28})$alkyl, $(C_2-C_{28})$alkenyl or $(C_2-C_{28})$alkynyl of Y is optionally substituted with one or more groups independently selected from halogen, $OR^d$ and $NR^d{}_2$;

W is O or S;

each $R^a$ is independently selected from H and $(C_1-C_6)$ alkyl;

each $R^b$ is independently selected from H and $(C_1-C_6)$ alkyl;

each $R^c$ is independently selected from H and $(C_1-C_6)$ alkyl; and each $R^d$ is independently selected from H and $(C_1-C_6)$ alkyl;

or a salt thereof.

A specific compound of formula I is:

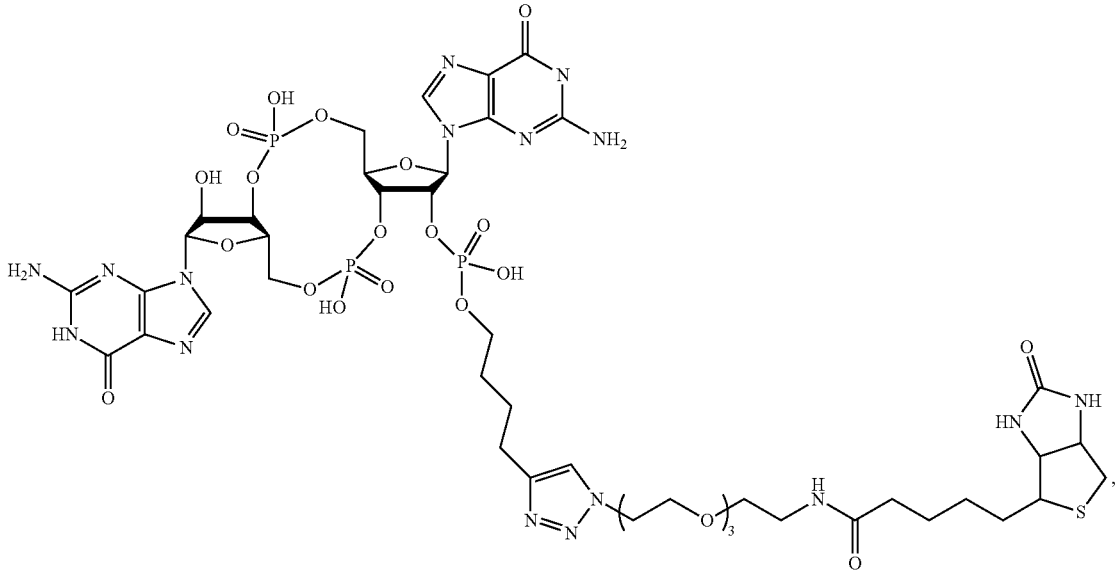

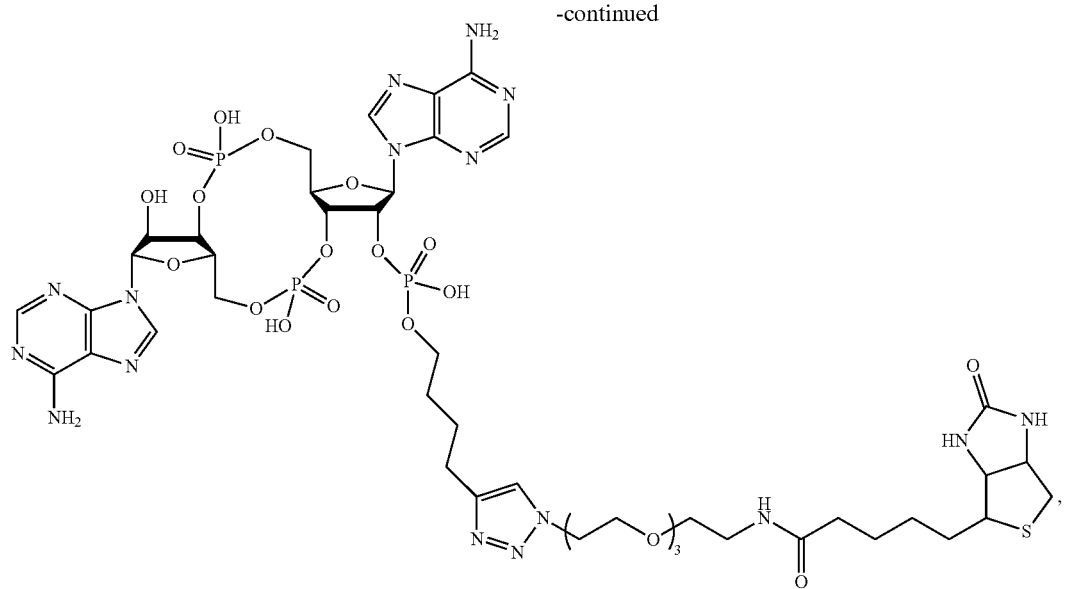
or a salt thereof.
A Specific Compound of Formula I is a Compound of Formula Ia':
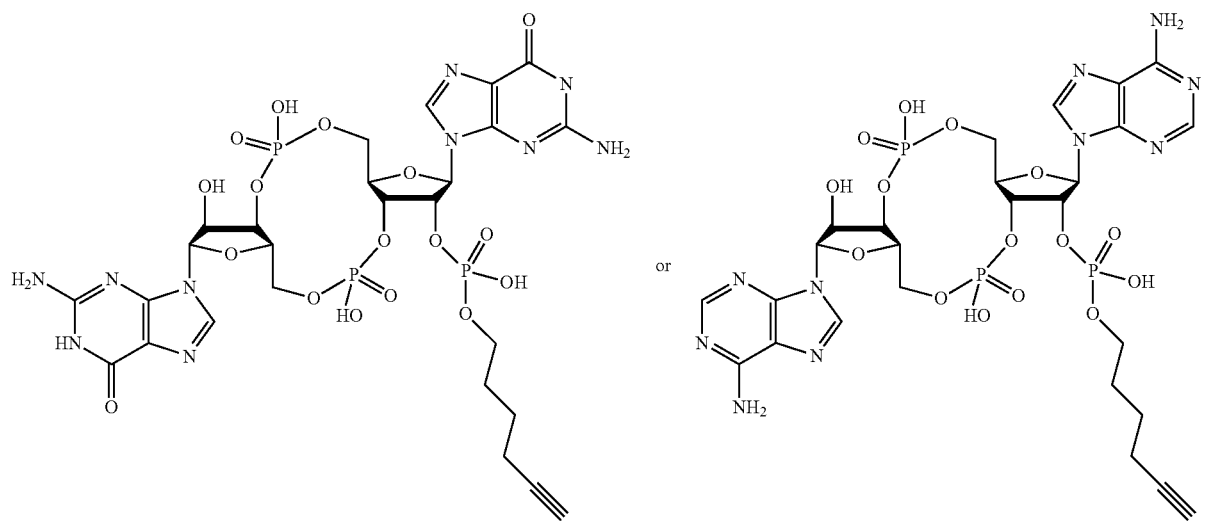
or a salt thereof.
In one embodiment
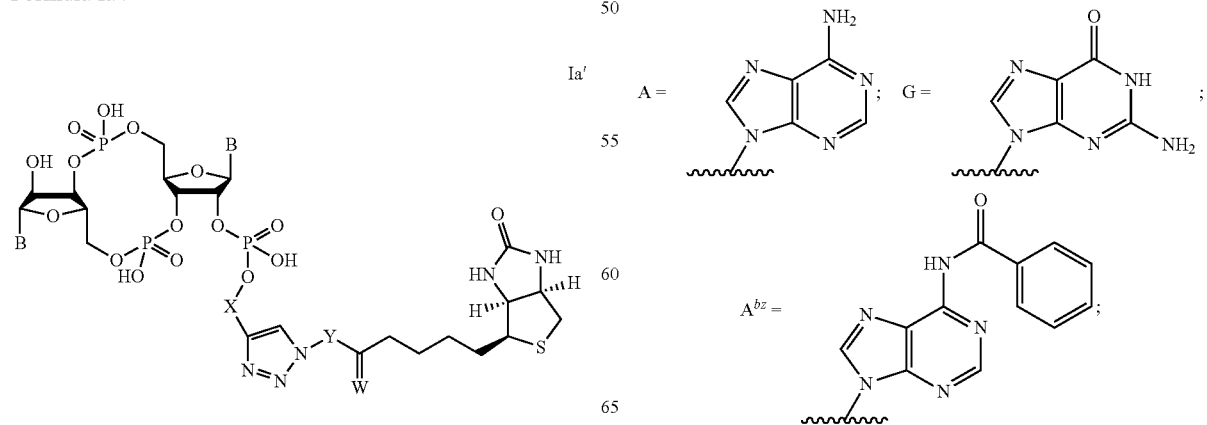

$G^{ib}=$ 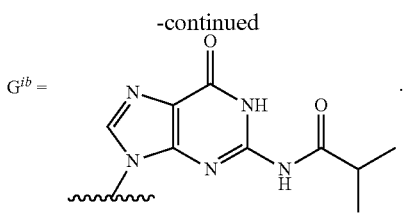

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In one embodiment the pharmaceutically acceptable salt is $Li^+$ or $^+N(R^x)_4$ wherein each $R^x$ is independently selected from H and $(C_1-C_8)$alkyl.

In one embodiment the pharmaceutically acceptable salt is $Li^+$ or $^+NH(CH_2CH_3)_3$.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

Certain embodiments of the invention will now be illustrated by the following non-limiting Example(s).

Example 1

A previously described one-flask route to c-di-GMP (Gaffney, B. L.; Veliath, E.; Zhao, J.; Jones, R. A., One-flask syntheses of c-di-GMP and the [Rp,Rp] and [Rp,Sp] thiophosphate analogues. *Org. Lett.* 2010, 12, 3269-3271) started with standard commercial N-ib-2'-O-TBS-5'-β-DMT guanosine phosphoramidite, 1a. In brief, as shown in Scheme 1, one portion was converted to the H-phosphonate and detritylated with trichloroacetic acid to give N-ib-2'-O-TBS-guanosine 3'-H-phosphonate, 2a. Quenching of the acid with pyridine generated pyridinium trichloroacetate which, along with the pyridinium trifluoroacetate from the previous step, catalyzed the subsequent amidite coupling. After the amidite coupling of 2a to a second portion of 1a, followed by oxidation and detritylation, the resulting linear dimer, 3a, was cyclized by an H-phosphonate coupling and oxidized to give 4a. To prepare 6a, first the single cyanoethyl group was removed, and the resulting symmetric product, 5a, was readily crystallized. This pure intermediate was then fully deprotected and precipitated/crystallized to give 6a.

The strategy reported herein on the synthesis of biotinylated c-di-GMP, as shown in Scheme 2, was to perform a monodesilylation of 4a, while retaining the cyanoethyl group for good chromatographic behavior and reasonable solubility in organic solvents. The resulting intermediate, 7a, could then be reacted with hexynyl phosphoramidite with minimal side reactions. A portion of 4a was prepared from 1a according to Scheme 1, and then purified by silica chromatography. Similar chromatography has been used to separate dithiophosphate diastereomers (Gaffney, B. L.; et al., *Org. Lett.* 2010, 12, 3269-327), but here the two diastereomers were combined to give 4a in 45% yield from 1a. Monodesilylation of 4a was then carried out, using only enough pyridine.HF to give about 50% of 7a and 10% full desilylation, leaving about 40% of starting 4a. Silica chromatography of the mixture gave reasonably pure 7a as four isomers, and the recovered 4a, which could later be reused.

Commercial hexynyl phosphoramidite (4.5 equiv) was reacted with 7a to give 8a. Silica chromatography gave a reasonably pure mixture of eight isomers, which was then fully deprotected with $CH_3NH_2$ followed by $Et_3N.3HF$ to give the dimer alkyne, 9a, as a single compound. Although the product was pure after semi-preparative RP chromatography, it was not completely the $Et_3NH^+$ salt, as found by NMR. Therefore, a new portion of 9a was prepared from 4a the same way, and then converted to the $Li^+$ salt, a non-volatile cation that does not favor guanine quartet assemblies. This 9a, $Li^+$ salt was used to determine a molar extinction coefficient of 22,700 OD $M^{-1}$ $cm^{-1}$. Assuming 9a, $Li^+$ and 9a, $Et_3NH^+$ salt have the same extinction coefficient, the yield for the original synthesis of 9a, $Et_3NH^+$ salt from 4a was determined to be 12%, taking into account the recovered 4a from the monodesilylation. The $Et_3NH^+$ salt of 9a was used in the subsequent click reaction, rather than the $Li^+$ salt, because of its better solubility in organic solvents.

Conditions were then optimized for the click reaction with commercial biotinylated azide. 1.5 equiv of the azide in the presence of 4 equiv of CuBr with 1.5 equiv (rel to CuBr) of the stabilizing ligand tris((1-benzyl-1H-1,2,3-triazol-4-yl)methyl)amine (TBTA) in a solvent mixture of 3:1 DMSO:tert-BuOH gave complete conversion by HPLC of 9a, $Et_3NH^+$ salt to the biotinylated c-di-GMP, 10a, after 20 h at room temperature. However, a significant amount of 10a was lost by associating with the TBTA that precipitated upon addition of $H_2O$. The completed reaction mixture was shook with a suspension of Amberlyte CG50 weak anion exchange resin in the same solvent for an hour to release the product, and then it was applied to a small column containing additional resin. The resulting solution was diluted with $H_2O$ and lyophilized. Purification by semi-preparative RP chromatography gave pure 10a, but again not completely the $Et_3NH^+$ salt. It was therefore converted to the Li+ salt and lyophilized to give 10a, Li+ salt in 43% isolated yield from 9a.

It is also reported here that c-di-AMP, 6b, can be prepared by the same one-flask procedure we used for c-di-GMP. The symmetric intermediate 5b was obtained in 28% yield from 1b, and c-di-AMP, 6b, was isolated in 81% yield from 5b, 23% yield from 1b. The only difference in the procedure was a longer time for the final removal of the TBS groups. In both cases, the use of an amidite coupling to prepare the linear dimer, followed by the extremely fast and specific H-phosphonate cyclization, is an ideal combination that gives a high-yield, scalable, and efficient set of reactions that do not require chromatography. In recent years, others have prepared c-di-AMP on fairly small scales using an amidite coupling with a phosphotriester cyclization (Smith, K. D.; Lipchock, S. V.; Livingston, A. L.; Shanahan, C. A.; Strobel, S. A., Structural and biochemical determinants of ligand binding by the c-di-GMP riboswitch. *Biochemistry* 2010, 49, 7351-7359; Suzuki, N.; Oyama, K.-i.; Tsukamoto, M., Practical synthesis of cyclic bis(3'-5')diadenylic acid (c-di-AMP). *Chem. Lett.* 2011, 40, 1113-1114), as well as phosphotriester reactions for both steps (Amiot, N.; Heintz, K.; Giese, B., New approach for the synthesis of c-di-GMP and its analogues. *Synthesis* 2006, 4230-4236).

In addition to the facile preparation of c-di-AMP, it is demonstrated and described here that its biotinylated conjugate, 10b, can be synthesized by the same method used for biotinylated c-di-GMP, 10a. The intermediate dimer alkynes described in this work, 9a/b, are versatile synthons and could readily be conjugated with longer biotinylated azides or even with azides linked to other functionalities. Certain embodiments of the invention are directed to the intermediate dimer alkynes described in this work, 9a and 9b, which is some embodiments are conjugated with longer biotinylated azides or with azides linked to other functionalities.

EXPERIMENTAL PROCEDURES

General Methods

5'-Hexyn-1-yl-(2-cyanoethyl)-(N,N-diisopropyl)-phosphoramidite and N-biotin-2-aminoethyl-diethyleneglycolyl-ethyl azide were purchased from Glen Research. CuBr and tris((1-benzyl-1H-1,2,3-triazol-4-yl)methyl)amine (TBTA) were purchased from Sigma-Aldrich. The DMSO and tert-BuOH used in the click reactions were both anhydrous. Benzoyl adenosine phosphoramidite was purchased from Thermo Fisher Scientific.

Analytical RP HPLC was performed on a Waters 2960 system with an Atlantis C18 column, 100° A, 4.6 mm×50 mm, 3 µm, using gradients of $CH_3CN$ and 0.1M aq $Et_3NHOAc$ (TEAA) (pH 6.8) at a flow rate of 1.0 mL/min. ESI-MS was acquired in negative mode using a Waters Micromass single quadrupole LCZ system. Normal phase purifications were done on disposable Varian SuperFlash SF25 cartridges at 10 mL/min. Semi-preparative RP HPLC purifications were performed on a Waters Novapak C18 19×300 mm column, using gradients of $CH_3CN$ and 0.1M aq $NH_4HCO_3$ (pH 6.8) at 6 mL/min. Li+ salts were obtained by passing samples through a small column (1.5 cm diameter) containing ~1 mL of AG 50W-X2 sulfonic acid resin, which had been converted to its Li+ form using LiOH.

Maximum UV absorbances were determined at 25° C. in the solvent indicated on an Aviv 14DS UV/VIS spectrophotometer. Molar extinction coefficients, $\epsilon$, were determined by dissolving a known mass of a lyophilized or precipitated sample in water in a volumetric flask, and measuring the absorbances of four diluted portions at 25° C. using different path length cells. The slope of a plot of absorbance/path length vs concentration gave the value of $\epsilon$. Masses for these molar extinction coefficient determinations, as well as for the final yields of 9a/b and 10a/b, were determined in Corning centrifuge tubes exposed to an anti-static U-electrode before weighing.

All NMR spectra were acquired on a Varian VNMRS 500 MHz spectrometer at 25° C. in the solvents specified. Samples were heated to 50° C. for ten min prior to acquisition. The $^1H$ and $^{13}C$ spectra in $d_6$-DMSO were referenced to that solvent, while those in $D_2O$ were referenced indirectly to 3-(trimethylsilyl)-1-propane-sulfonic acid, sodium salt. The $^1H$ spectra in $D_2O$ were acquired with frequency presaturation for water suppression, and therefore the resonances adjacent to 4.8 ppm are diminished. The $^{31}P$ spectra were referenced indirectly to neat phosphoric acid.

One-Flask Synthesis of 4a

A portion of 4a was prepared following a previously published procedure (Gaffney, B. L.; et al., *Org. Lett.* 2010, 12, 3269-327), starting with 3.00 mmol of 1a. Both diastereomers of 4a were purified together on 80 g of silica gel, using a gradient of 0 to 25% $CH_3OH$ in $CH_2Cl_2$, to give 1.615 g of 4a (1.36 mmol, 45% from 1a), which was characterized as follows: m/z (M-H) 1110 (calculated for $C_{43}H_{66}N_{11}O_{16}P_2Si_2^-$: 1110); UV ($CH_3OH$) $\lambda_{max}$ 255 nm; $^1H$ NMR ($d_6$-DMSO): $\delta$ (extra resonances indicate aggregation) 12.22-11.61 (8s, 8H), 8.39-8.17 (4s, 4H), 7.79 (br, 3H), 6.03-5.85 (4d, 4H), 5.32-4.02 (m, 20H), 3.03-2.67 (m, 8H), 1.22-1.06 (m, 37H), 0.87-0.65 (4s, 36H), 0.10-0.15 (8s, 24H); $^{13}C$ NMR ($d_6$-DMSO) 25° C.: $\delta$ 180.2, 180.0, 154.8, 154.7, 149.2, 148.8, 148.4, 148.2, 120.7, 119.8, 119.7, 118.0, 117.9, 86.4, 86.3, 85.1, 84.8, 83.9, 80.4, 72.4, 62.9, 62.8, 62.7, 56.0, 54.8, 51.0, 46.2, 34.9, 34.8, 34.7, 34.6, 27.1, 25.8, 25.4, 25.3, 18.9, 18.8, 18.7, 17.8, 17.7, 17.5, −3.2, −4.9, −5.1, −5.2, −5.5, −5.6, −5.8; $^{31}P$ NMR ($d_6$-DMSO) 25° C.: $\delta$ (extra resonances indicate aggregation) 1.40, 1.26, 0.91, −2.34.

Monodesilylation to Give 7a

To a portion of 4a (0.795 g, 0.671 mmol) in a 50 mL plastic centrifuge tube with a short stir bar was added 18 mL of dry $CH_3CN$. To the stirring suspension was added pyridine.HF (0.128 mL, 4.93 mmol, 7.3 equiv). The mixture was stirred for 18 h. The stir bar was removed, silica gel (100 mg) was added, and the tube was shaken for 30 min to consume excess $F^-$. The mixture was filtered through a sintered glass funnel, and the silica gel washed 4× with 6 mL portions of 20% $CH_3OH$ in $CH_2Cl_2$. The filtrate was concentrated to about 1 mL (not dryness), and 3 mL of $CH_2Cl_2$ was added. This mixture was purified on 60 g of silica gel, using a gradient of 2 to 30% $CH_3OH$ in $CH_2Cl_2$, to give 0.211 g of nearly pure 7a as a mixture of four isomers, m/z (M-H) 996 (calculated for $C_{37}H_{52}N_{11}O_{16}P_2Si^-$: 996), and 0.313 g of recovered 4a. This 7a was used as follows without further purification.

Coupling to Give Protected Dimer Alkyne, 8a

To 7a (0.211 g) from above in a 100 mL RBF with a stir bar was added pyridinium trifluoroacetate (0.485 g, 2.51 mmol, 3 equiv rel to amidite). The mixture was dried 3× by evaporation of $CH_3CN$, never letting it go dry, and ending with ~3 mL. The flask was sealed with a septum, then evacuated and refilled 10× with dry $N_2$. 5'-Hexyn-1-yl-(2-cyanoethyl)-(N,N-diisopropyl)-phosphoramidite (0.25 g, 0.838 mmol, ~4.6 equiv) in a sealed bottle was dissolved by addition of 1.5 mL of dry $CH_3CN$ through the septum, and the contents were then transferred to the flask. The solution was stirred for 30 min, and 5.5M tert-butyl hydroperoxide (0.46 mL, 2.51 mmol, 3 equiv rel to amidite) was added. The solution was stirred for 30 min, then concentrated and purified on 40 g of silica gel, using a gradient of 0 to 20% $CH_3OH$ in $CH_2Cl_2$, to give 0.170 g of nearly pure 8a as a mixture of eight isomers. This 8a was used as follows without further purification.

Deprotection to Give Dimer Alkyne, 9a

To 8a (0.170 g) from above in a 100 mL RBF with a stir bar was added 10 mL (80 mmol, ~300 equiv rel to each ib) of $CH_3NH_2$ in anhydrous EtOH (33% by weight). After 3 h, the mixture was concentrated to dryness. Pyridine (3 mL) and $Et_3N$ (2 mL) were added and the mixture was concentrated to an oil. This process was repeated two more times to convert the tert-$BuNH_3^+$ to the $Et_3NH^+$ salt. Pyridine (2 mL) was added and the flask with a vent needle was placed in an oil bath at 55° C., and the contents stirred for 5 min. $Et_3N$ (1.4 mL) and $Et_3N\cdot 3HF$ (0.8 mL, 14.7 mmol $F^-$, ~110 equiv) were added simultaneously through separate syringes. Caution, HF: rinse all needles, syringes, septa, etc with aq $K_2CO_3$ before discarding. The solution was stirred for 1 h, with occasional swirling. The flask was then removed from the oil bath and placed on a different stir plate. HPLC grade acetone (25 mL) was added in a slow stream over 1 min, and the resulting suspension of white solid was stirred for 15 min. The product was collected by filtration in a sintered glass funnel, washed 3× with 5 mL of acetone, and dried in a desiccator overnight over KOH. The product was then dissolved in 2 mL of 0.1M $NH_4HCO_3$ and purified by semi-preparative RP chromatography, using a gradient of 2 to 40% $CH_3CN$ in 0.1M $NH_4HCO_3$, to give pure 9a (0.0445 g) as primarily the $Et_3NH^+$ salt.

Another portion of 9a was prepared from 4a by the same method and was then converted to the $Li^+$ salt. This second portion, 9a, $Li^+$ (0.0344 g, 0.0396 mmol), was used to determine a molar extinction coefficient of 22,700 OD $M^{-1}$ $cm^{-1}$. Assuming that 9a, $Et_3NH^+$ and 9a, $Li^+$ have the same extinction coefficient, the original preparation of 9a, $Et_3NH^+$ was determined by UV to be 0.0500 mmol, 12% from 4a, taking into account the recovered 4a from the monodesilylation step. The $Li^+$ salt of 9a was characterized as follows: m/z (M-H) 849 (calculated for $C_{26}H_{32}N_{10}O_{17}P_3^-$: 849); UV ($H_2O$) $\lambda_{max}$ 253 nm, $\epsilon$=22,700 OD $M^{-1}$ $cm^{-1}$; $^1H$ NMR ($D_2O$): δ 7.99 (s, 1H), 7.98 (s, 1H), 5.93 (s, 1H), 5.70 (s, 1H), 5.33-5.27 (m, 1H), 5.12-5.00 (m, 2H), 4.41-4.25 (m, 4H), 3.99-3.84 (m, 41-1), 2.17-2.06 (m, 3H), 1.66-1.56 (m, 2H), 1.52-1.41 (m, 2H); $^{13}C$ NMR ($D_2O$): δ 158.8, 158.6, 156.5, 156.4, 152.2, 151.5, 139.3, 138.7, 116.6, 116.3, 93.2, 91.4, 88.6, 83.2, 82.9, 78.4, 75.7, 72.6, 71.9, 71.7, 68.7, 64.8, 64.6, 31.6, 31.5, 26.8; $^{31}P$ NMR ($D_2O$): δ 0.14, -0.47, -1.17.

Click Conjugation to Give Biotinylated c-Di-GMP, 10a

A portion of 9a, $Et_3NH^+$ (0.0160 mmol determined by UV) was lyophilized in a 15 mL centrifuge tube. The tube was evacuated and refilled 10× with Ar in a small desiccator. A 3:1 mixture of DMSO:tert-BuOH (2.0 mL) was added by syringe to a 0.025 mmol sealed bottle of N-biotin-2-aminoethyl-diethyleneglycolyl-ethyl azide to make a 0.0125M solution. This entire solution was transferred by syringe to the lyophilized 9a, and the mixture was vortexed until it all dissolved. CuBr (0.0092 g, 0.064 mmol, 4 equiv rel to 9a) was weighed into a 15 mL centrifuge tube pre-filled with Ar. A 3:1 mixture of DMSO:tert-BuOH (0.94 mL) was added to a 50 mg bottle of tris((1-benzyl-1H-1,2,3-triazol-4-yl)methyl)amine (TBTA, 0.0942 mmol, 1.47 equiv rel to CuBr) to make a 0.10M solution. The bottle was evacuated and refilled 10× with Ar, and the solution was then transferred by syringe to the tube of CuBr. This tube was vortexed, then evacuated and refilled 10× with Ar. The CuBr/TBTA solution was transferred using a glass pipet under a flow of Ar to the tube containing 9a/azide. This final tube was vortexed and left at room temperature.

After 20 h, a thick suspension of Amberlyte CG50 anion exchange resin was prepared in 3:1 DMSO:tert-BuOH, and ~2 mL (3.0 meq) was added to the tube containing crude 10a, which was shaken for 1 h. Another 2 mL portion of the resin suspension was placed in a small column (1.5 cm diameter) and allowed to drain. The reaction mixture was then applied to this column and collected in a 50 mL centrifuge tube. The column was washed 15× with 1 mL portions of $H_2O$. The collected solution was divided among four 50 mL centrifuge tubes, diluted further with water, and lyophilized. Water (1 mL) was added to one of the tubes, the solid was scraped from the walls of the tube with a spatula, and the mixture was transferred in turn to each of the other tubes, with scraping. The final mixture was filtered through a 25 mm×0.45 µm filter into a new 50 mL centrifuge tube. The original tubes were rinsed and scraped sequentially 10× with 1 mL portions of $H_2O$, with each rinse filtered. The solution of crude 10a in the final tube was lyophilized.

Crude 10a was purified by semi-preparative RP chromatography to give pure 10a, primarily as the $Et_3NH^+$ salt. This product was converted to the $Li^+$ salt, to give 10a, $Li^+$ (0.00895 g, 0.00682 mmol, 43% from 9a), which was characterized as follows: m/z (M-H) 1293 (calculated for $C_{44}H_{64}N_{16}O_{22}P_3S^-$: 1293); UV ($H_2O$) $\lambda_{max}$ 253 nm, $\epsilon$=18, 100 OD $M^{-1}$ $cm^{-1}$; $^1H$ NMR ($D_2O$): δ 7.96 (s, 1H), 7.93 (s, 1H), 7.63 (s, 1H), 6.06 (s, 1H), 5.87 (s, 1H), 5.12-5.05 (m, 1H), 4.95-4.87 (m, 1H), 4.84-4.75 (s, 1H), 4.65-4.57 (m, 2H), 4.49-4.38 (m, 3H), 4.32-4.15 (m, 4H), 4.02-3.93 (m, 2H), 3.86-3.75 (m, 4H), 3.54-3.38 (m, 10H), 3.23 (t, J=5 Hz, 2H), 3.15-3.07 (m, 2H), 2.82 (dd, J=13 Hz, 5 Hz, 1H), 2.62 (d, J=13 Hz, 1H), 2.54 (t, J=7 Hz, 1H), 2.10 (t, J=7 Hz, 2H), 1.61-1.33 (m, 8H), 1.27-1.15 (m, 2H); $^{13}C$ NMR ($D_2O$): δ 177.0, 165.5, 159.0, 154.1, 153.9, 148.5, 137.5, 123.5, 116.7, 116.3, 89.2, 87.7, 80.0, 76.1, 73.6, 71.0, 70.0, 69.9, 69.8, 69.7, 69.6, 69.0, 66.2, 62.2, 60.4, 55.5, 50.1, 39.9, 39.1, 39.0, 35.6, 29.4, 28.0, 27.9, 25.3, 24.3; $^{31}P$ NMR ($D_2O$): δ 0.29, -0.43, -0.92.

One-Flask Synthesis of 4b

A portion of adenosine phosphoramidite, 1b (2.57 g, 2.60 mmol, 1.3 equiv), was dried 3× by evaporation of 16 mL of dry $CH_3CN$, the last time leaving 8 mL. Four 3 Å molecular sieves were added. To a $2^{nd}$ portion of 1b (1.98 g, 2.00 mmol) dissolved in 10 mL of $CH_3CN$ and water (0.072 mL, 4 mmol, 2 equiv) was added pyridinium trifluoroacetate (0.464 g, 2.4 mmol, 1.2 equiv). After 1 min, 10 mL of tert-$BuNH_2$ was added. After another 10 min, the mixture was concentrated to a foam, the residue was dissolved in 20 mL of $CH_3CN$, and concentrated again to a foam. This addition and concentration were repeated one more time. To the residue dissolved in 24 mL of $CH_2Cl_2$ was added $H_2O$ (0.360 mL, 20 mmol, 10 equiv), followed by 24 mL of 6% dichloroacetic acid (DCA, 17.6 mmol) in $CH_2Cl_2$. After 10 min, the reaction was quenched by addition of pyridine (2.8 mL, 35 mmol, 2 equiv rel to DCA). The mixture was then concentrated, and the residue was dissolved in 16 mL of $CH_3CN$ and concentrated again. This process was repeated two more times, the last time leaving 2b in 5 mL.

To the above solution of 2b was added the dried solution of 1b using a syringe with a bent needle (to access as much of the solution as possible). After 2 min, anhydrous tert-butyl hydroperoxide 5.5M in decane (1.1 mL, 6 mmol, 3 equiv) was added. After 30 min, the solution was cooled in an ice bath, and 0.50 g of $NaHSO_3$ dissolved in 1 mL $H_2O$ was added. The ice bath was immediately removed, the mixture was stirred for 5 min, and then concentrated to a small volume. The residual oil was dissolved in 32 mL of $CH_2Cl_2$, followed by addition of $H_2O$ (0.36 mL, 20 mmol, 10 equiv) and then 32 mL of 6% DCA (23 mmol) in $CH_2Cl_2$. After 10 min, the reaction was quenched with 20 mL of pyridine. The mixture was concentrated to a small volume, 60 mL more pyridine was added, and the solution was concentrated again, leaving 3b in 40 mL.

To the above solution of 3b was added 5,5-dimethyl-2-oxo-2-chloro-1,3,2-dioxaphosphinane (DMOCP, 1.36 g of 95% reagent, 7 mmol, 3.5 equiv). After 10 min, the reaction was quenched by addition of $H_2O$ (1.28 mL, 70 mmol, 10 equiv rel to DMOCP), and $I_2$ (0.66 g, 2.6 mmol, 1.3 equiv) was added immediately. After 5 min, the mixture was poured into 280 mL of $H_2O$ containing 0.4 g $NaHSO_3$. After 5 min of stirring, 8 g of $NaHCO_3$ was slowly added. After 5 min more of stirring, the aqueous solution was partitioned with 320 mL 1:1 $EtOAc:Et_2O$. The separated aqueous layer was then partitioned with an additional 80 mL of 1:1 $EtOAc:Et_2O$. The organic layers were combined and concentrated to an oil, with excess pyridine removed by evaporation of three 15 mL portions of EtOAc.

The above oil was dissolved in $CH_2Cl_2$ and purified on 80 g of silica gel, using a gradient of 0 to 20% $CH_3OH$ in $CH_2Cl_2$. Pure fractions of both diastereomers were combined together, concentrated to a foam, and dried in a desiccator over KOH overnight, giving 4b (1.079 g, 0.884 mmol, 44% from 1b), which was characterized as follows: m/z (M-H) 1146 (calculated for $C_{49}H_{62}N_{11}O_{14}P_2Si_2^-$: 1146; UV ($CH_3OH$) $\lambda_{max}$ 280 nm; $^1$H NMR ($d_6$-DMSO): δ (extra resonances indicate aggregation) 11.26-11.04 (4s, 4H), 8.85-8.54 (8s, 8H), 8.08-7.92 (m, 8H), 7.67-7.50 (m, 12H), 6.18-6.03 (4d, 4H), 5.37-4.08 (m, 20H), 3.04-2.82 (m, 4H), 1.16-0.98 (m, 13H), 0.86-0.71 (4s, 36H), 0.16-0.12 (8s, 24H); $^{13}$C NMR ($d_6$-DMSO): δ 165.6, 151.8, 151.7, 151.3, 150.5, 150.4, 150.2, 142.7, 142.2, 133.3, 132.5, 129.1, 128.8, 128.5, 125.8, 125.5, 118.1, 118.0, 117.9, 88.3, 80.3, 74.9, 73.9, 73.2, 71.9, 71.4, 63.2, 63.1, 63.0, 62.9, 62.8, 62.7, 50.8, 46.0, 25.8, 25.7, 25.6, 25.5, 25.4, 19.1, 18.5, 18.4, 17.8, 17.6, 17.5, −3.2, −4.4, −5.0, −5.1, −5.2, −5.4, −5.5, −5.6; $^{31}$P NMR ($d_6$-DMSO): δ (extra resonances indicate aggregation) 0.20, −0.08, −1.09, −2.81.

One-Flask Synthesis of 5b

Another portion of 4b was prepared from 1b as above on a 2.65 mmol scale. Instead of chromatography, one-half of the organic solution containing 4b was dissolved in 10 mL $CH_3CN$ and converted to 5b by addition of 10 mL of tert-$BuNH_2$. After 10 min, the mixture was concentrated to a foam, the residue was dissolved in 10 mL of $CH_3CN$, and concentrated again. This addition and concentration were repeated one more time. The residue was then dissolved in 10 mL of $CH_3OH$, filtered, and concentrated to a foam. The product was crystallized by addition of 10 mL of $CH_2Cl_2$, collected by filtration, washed with minimal $CH_2Cl_2$, and dried in a desiccator over KOH overnight, giving pure 5b (0.467 g, 0.376 mmol, 28% from 1.32 mmol of 1b), which was characterized as follows: m/z (M-H) 1093 (calculated for $C_{46}H_{59}N_{10}O_{14}P_2Si_2^-$: 1093); UV ($CH_3OH$) $\lambda_{max}$ 280 nm; $^1$H NMR ($d_6$-DMSO): δ 11.31 (br, 1H), 8.89 (s, 1H), 8.73 (s, 1H), 8.02, (d, J=8 Hz, 2H), 7.64-7.58 (m, 1H), 7.49 (t, J=8 Hz, 2H), 6.05 (s, 1H), 4.66-4.57 (m, 1H), 4.46-4.40 (m, 1H), 4.21-4.14 (m, 1H), 4.14-4.05 (m, 1H), 3.82-3.74 (m, 1H), 0.98 (s, 9H), 0.97 (s, 9H), 0.26 (s, 3H), 0.22 (s, 3H); $^{13}$C NMR ($d_6$-DMSO): δ 165.6, 151.7, 151.3, 149.9, 141.5, 133.2, 132.4, 128.5, 128.3, 124.9, 89.7, 76.0, 74.5, 69.4, 61.5, 50.6, 26.8, 25.9, 17.9, −4.2, −5.1; $^{31}$P NMR ($d_6$-DMSO): δ −3.08.

c-di-AMP, 6b

To a portion of 5b (0.443 g, 0.357 mmol) in a 250 mL RBF was added 25 mL of $CH_3NH_2$ in anhydrous EtOH (33% by weight, 200 mmol, 280 equiv rel to each benzoyl). After 1 h at room temperature, the mixture was concentrated to an oil, to which 3 mL of pyridine and 1 mL of $Et_3N$ were added. The mixture was concentrated to an oil, and this process was repeated two more times to convert the tert-$BuNH_3^+$ to the $Et_3NH^+$ salt. To the oil was added 10 mL of pyridine, and the flask with a vent needle was placed in an oil bath at 55° C. $Et_3N$ (4.4 mL) and $Et_3N.3HF$ (2.6 mL, 48 mmol $F^-$, 67 eq rel to each TBS) were added simultaneously through two syringes. Caution, HF: rinse all needles, syringes, septa, etc with aq $K_2CO_3$ before discarding. The mixture was swirled and then stirred at 55° C. After 20 h, the flask was removed from the oil bath and placed on a different stir plate. HPLC grade acetone (200 ml) was immediately added in a slow stream over 1 min to the stirring mixture. After 10 min, the solid was collected by filtration, washed 5× with 5 mL portions of acetone, and dried in a desiccator over KOH overnight, giving pure 6b (0.247 g, 0.288 mmol, 81% from 5b, 23% from 1b), which was characterized as follows: mp 196-198° C. dec; m/z (M-H) 657 (calculated for $C_{20}H_{23}N_{10}O_{12}P_2^-$: 657); UV ($CH_3OH$) $\lambda_{max}$ 258 nm, $\epsilon$=18, 600 OD $M^{-1}$ $cm^{-1}$; $^1$H NMR ($d_6$-DMSO): δ 8.22 (s, 1H), 7.82 (s, 1H), 5.99 (s, 1H), 4.83-4.72 (m), 4.67-4.65 (s), 4.43-4.34 (m, 2H), 4.07-3.97 (m, 1H), 3.05 (q, J=7 Hz, 12H), 1.13 (t, J=7 Hz, 18H); NMR ($d_6$-DMSO): δ 157.2, 154.7, 149.3, 141.0, 120.8, 92.7, 82.4, 76.4, 72.7, 64.9, 49.3, 10.8; $^{31}$P NMR ($d_6$-DMSO): δ −0.83.

Monodesilylation to Give 7b

To a portion of 4b (0.488 g, 0.400 mmol) in a 50 mL plastic centrifuge tube with a short stir bar was added 15 mL of dry $CH_3CN$. To the stirring suspension was added pyridine.HF (0.160 mL, 6.16 mmol, 15.4 equiv). The mixture was stirred for 18 h. The stir bar was removed, silica gel (50 mg) was then added, and the tube was shaken for 30 min to consume excess $F^-$. The mixture was filtered through a sintered glass funnel, and the silica gel washed 4× with 6 mL portions of 20% $CH_3OH$ in $CH_2Cl_2$. The filtrate was concentrated to about 10 mL, 5 mL of pyridine was added, and the mixture was concentrated to an oil. Additional $CH_2Cl_2$ was added (10 mL) and the mixture concentrated once more. Then 3 mL of $CH_2Cl_2$ was added and the mixture was purified on 60 g of silica gel, using a gradient of 2 to 30% $CH_3OH$ in $CH_2Cl_2$, to give 0.137 g of nearly pure 7b as a mixture of four isomers, ink (M-H) 1032 (calculated for $C_{43}H_{48}N_{11}O_{14}P_2Si^-$: 1032), and 0.086 g of recovered 4b. This 7b was used as follows without further purification.

Coupling to Give Protected Dimer Alkyne, 8b

To 7b (0.137 g) from above in a 100 mL RBF with a stir bar was added pyridinium trifluoroacetate (0.970 g, 5.03 mmol, 3 equiv rel to amidite). The mixture was dried 3× by evaporation of $CH_3CN$, never letting it go dry, and ending with ~3 mL. The flask was sealed with a septum, then evacuated and refilled 10× with dry $N_2$. 5'-Hexyn-1-yl-(2-cyanoethyl)-(N,N-diisopropyl)-phosphoramidite (0.50 g, 1.68 mmol, ~13.5 equiv) in two sealed bottles was dissolved by addition of 1.5 mL of dry $CH_3CN$ through the septum of the first bottle, the contents transferred to the second bottle, and then to the flask. The solution was stirred for 45 min, and 5.5M tert-butyl hydroperoxide (1.22 mL, 6.72 mmol, 4 equiv rel to amidite) was added. The solution was stirred for 40 min, then concentrated, and purified on 40 g of silica gel, using a gradient of 0 to 25% $CH_3OH$ in $CH_2Cl_2$, to give 8b as a mixture of eight isomers. This 8b was used as follows without further purification.

Deprotection to Give Dimer Alkyne, 9b

To 8b from above in a 100 mL RBF with a stir bar was added 18 mL (144 mmol, ~180 equiv rel to each bz) of $CH_3NH_2$ in anhydrous EtOH (33% by weight). After 3 h, the mixture was concentrated to dryness. Pyridine (3 mL) and $Et_3N$ (2 mL) were added and the mixture was concentrated to an oil. This process was repeated two more times to convert the tert-$BuNH_3^+$ to the $Et_3NH^+$ salt. Pyridine (2 mL) was added and the flask with a vent needle was placed in an oil bath at 55° C., and stirred for 5 min. $Et_3N$ (3.0 mL) and $Et_3N.3HF$ (1.9 mL, 35 mmol $F^-$, ~85 equiv) were added simultaneously through separate syringes. Caution, HF: rinse all needles, syringes, septa, etc with aq $K_2CO_3$ before discarding. The solution was stirred overnight. The flask was then removed from the oil bath and placed on a different stir plate. HPLC grade acetone (95 mL) was added over 1 min, and the resulting suspension of white solid was stirred for 15 min. The product was collected by filtration in a sintered glass funnel, washed 3× with 5 mL of acetone, and dried in a desiccator overnight over KOH. The product was then dissolved in 2 mL of 0.1M $NH_4HCO_3$ and purified by semi-preparative RP chromatography, using a gradient of 2 to 40% $CH_3CN$ in 0.1M $NH_4HCO_3$, to give pure 9b (9.51 mg) as primarily the $Et_3NH^+$ salt.

Another portion of 9b was prepared from 4b by the same method and was then converted to the $Li^+$ salt. This second portion, 9b, $Li^+$ (0.0755 g, 0.00903 mmol), was used to determine an extinction coefficient of 25,000 OD $M^{-1}$ $cm^{-1}$. Assuming that 9b, $Et_3NH^+$ and 9b, $Li^+$ have the same extinction coefficient, the original preparation of 9b, $Et_3NH^+$ was determined by UV to be 0.0102 mmol, 3% from 4b, taking into account the recovered 4b from the monodesilylation. The $Li^+$ salt of 9b was characterized as follows: m/z (M-H) 817 (calculated for $C_{26}H_{32}N_{10}O_{15}P_3^-$: 817); UV ($H_2O$) $\lambda_{max}$ 258 nm, $\epsilon$=25,000 OD $M^{-1}$ $cm^{-1}$; $^1H$ NMR ($D_2O$): δ 8.44 (s, 1H), 8.43 (s, 1H), 8.21 (s, 1H), 8.20 (s, 1H), 6.43 (s, 1H), 6.19 (s, 1H), 5.22-5.16 (m, 1H), 4.59-4.41 (m, 4H), 4.18-4.01 (m, 4H), 2.37-2.22 (m, 3H), 1.82-1.72 (m, 2H), 1.67-1.57 (m, 2H); $^{13}C$ NMR ($D_2O$): δ 153.2, 152.6, 149.9, 148.9, 147.7, 147.4, 140.6, 139.9, 118.5, 118.4, 89.9, 88.1, 86.2, 79.8, 79.7, 76.9, 74.0, 70.3, 69.4, 66.4, 62.3, 62.6, 29.3, 29.2, 24.4, 17.5; $^{31}P$ NMR ($D_2O$): δ 0.37, -0.68, -1.30.

Click Conjugation to Give Biotinylated c-Di-AMP, 10b

A portion of 9b, $Et_3NH^+$ (0.00500 mmol determined by UV) was lyophilized in a 15 mL centrifuge tube. The tube was evacuated and refilled 10× with Ar in a small desiccator. A 3:1 mixture of DMSO:tert-BuOH (2.5 mL) was added by syringe to a 0.025 mmol sealed bottle of N-biotin-2-aminoethyl-diethyleneglycolyl-ethyl azide to make a 0.0100M solution. A portion of this solution (1.0 mL, 0.010 mmol, 2.0 equiv) was transferred by syringe to the lyophilized 9b, and the mixture was vortexed until it all dissolved. CuBr (0.0072 g, 0.050 mmol, 10 equiv rel to 9b) was weighed into a 15 mL centrifuge tube pre-filled with Ar. A 3:1 mixture of DMSO:tert-BuOH (0.94 mL) was added to a 50 mg bottle of TBTA (0.0942 mmol) to make a 0.10M solution. The bottle was evacuated and refilled 10× with Ar. A portion of this solution (0.75 mL, 0.075 mmol, 1.5 equiv rel to CuBr) was then transferred by syringe to the tube of CuBr. This tube was vortexed, then evacuated and refilled 10× with Ar. The CuBr/TBTA solution was transferred using a glass pipet under a flow of Ar to the tube containing 9b/azide. This final tube was vortexed and left at room temperature.

After 20 h, a thick suspension of Amberlyte CG50 anion exchange resin was prepared in 3:1 DMSO:tert-BuOH, and ~2 mL (3.0 meq) was added to the tube containing 10b, which was shaken for 1 h. Another 2 mL portion of the resin suspension was placed in a small column (1.5 cm diameter) and allowed to drain. The reaction mixture was then applied to this column and collected in a 50 mL centrifuge tube. The column was washed 15× with 1 mL portions of $H_2O$. The collected solution was divided among four 50 mL centrifuge tubes, diluted further with water, and lyophilized. Water (1 mL) was added to one of the tubes, the solid was scraped from the walls of the tube with a spatula, and the mixture was transferred in turn to each of the other tubes, with scraping. The final mixture was filtered through a 25 mm×0.45 μm filter into a new 50 mL centrifuge tube. The original tubes were washed and scraped sequentially 10× with 1 mL of $H_2O$, with each rinse filtered. The solution of crude 10b in the final tube was lyophilized.

Three other portions of 9b (5.00, 7.45, and 9.00 mmol) were used to prepare additional crude 10b by the same procedure, which was combined with the first. This combined crude 10b was purified by semi-preparative RP chromatography to give pure 10b, primarily as the $Et_3NH^+$ salt. This product was converted to the $Li^+$ salt, to give 10b, $Li^+$ (0.01020 g, 0.0080 mmol, 30% from 0.0265 mmol of 9b), which was characterized as follows: m/z (M-H) 1261 (calculated for $C_{44}H_{64}N_{16}O_{20}P_3S^-$: 1261); UV ($H_2O$) $\lambda_{max}$ 259 nm, $\epsilon$=13,200; $^1H$ NMR ($D_2O$): δ 8.33-8.29 (2s, 2H), 8.02-7.95 (2s, 2H), 7.58 (s, 1H), 6.22 (s, 1H), 6.03 (s, 1H), 5.15-5.10 (m, 1H), 4.97-4.90 (m, 1H), 4.86-4.80 (m, 1H), 4.65-4.61 (m, 1H), 4.44-4.17 (m, 8H), 4.06-3.97 (m, 2H), 3.92-3.81 (m, 2H), 3.77 (t, J=5 Hz, 2H), 3.48-3.37 (m, 10H), 3.21 (t, J=5 Hz, 2H), 3.06 (p, J=4 Hz, 1H), 2.78 (dd, J=13 Hz, J=5 Hz, 1H), 2.62-2.45 (m, 3H), 2.07 (t, J=7 Hz, 2H), 1.55-1.31 (m, 8H), 1.22-1.12 (m, 2H); $^{13}C$ NMR ($D_2O$): δ 177.0, 167.8, 155.5, 155.4, 152.9, 152.8, 148.4, 148.3, 147.8, 139.9, 139.3, 123.4, 118.7, 118.6, 89.7, 87.5, 79.9, 79.7, 76.6, 73.9, 70.6, 70.5, 69.8, 69.7, 69.6, 69.0, 66.3, 66.2, 62.2, 60.4, 55.5, 50.0, 39.9, 39.1, 35.6, 29.4, 28.0, 27.8, 25.3, 25.0, 24.3; $^{31}P$ NMR ($D_2O$): δ 0.29, -0.43, -0.92

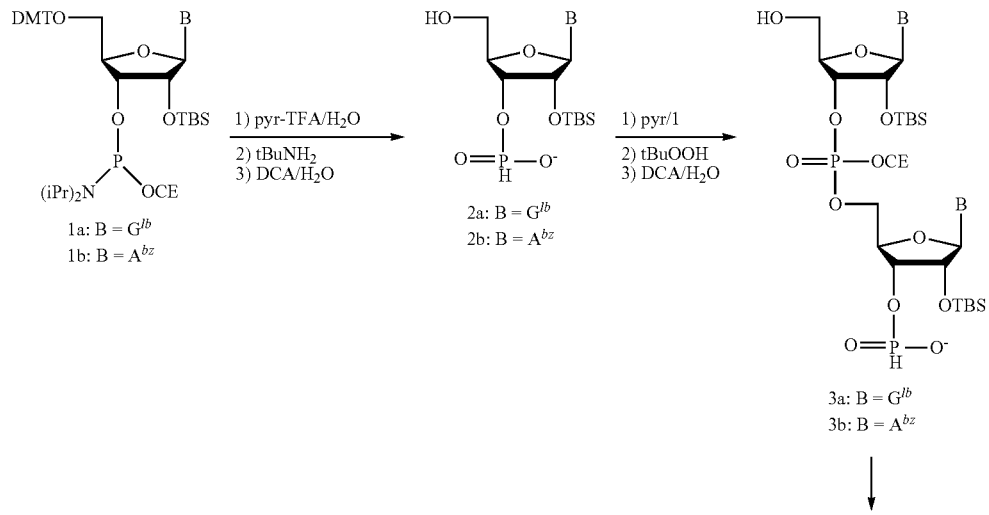

SCHEME 1 Synthesis of c-di-GMP and c-di-AMP from commercially available phosphoramidites 1a and 1b.

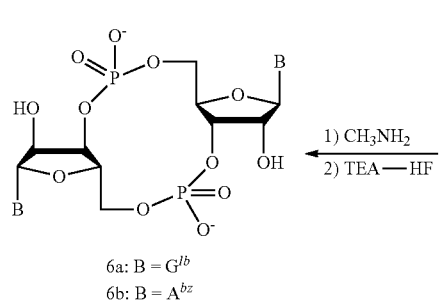
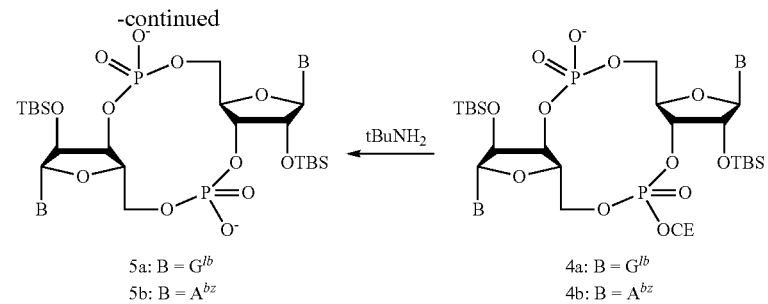
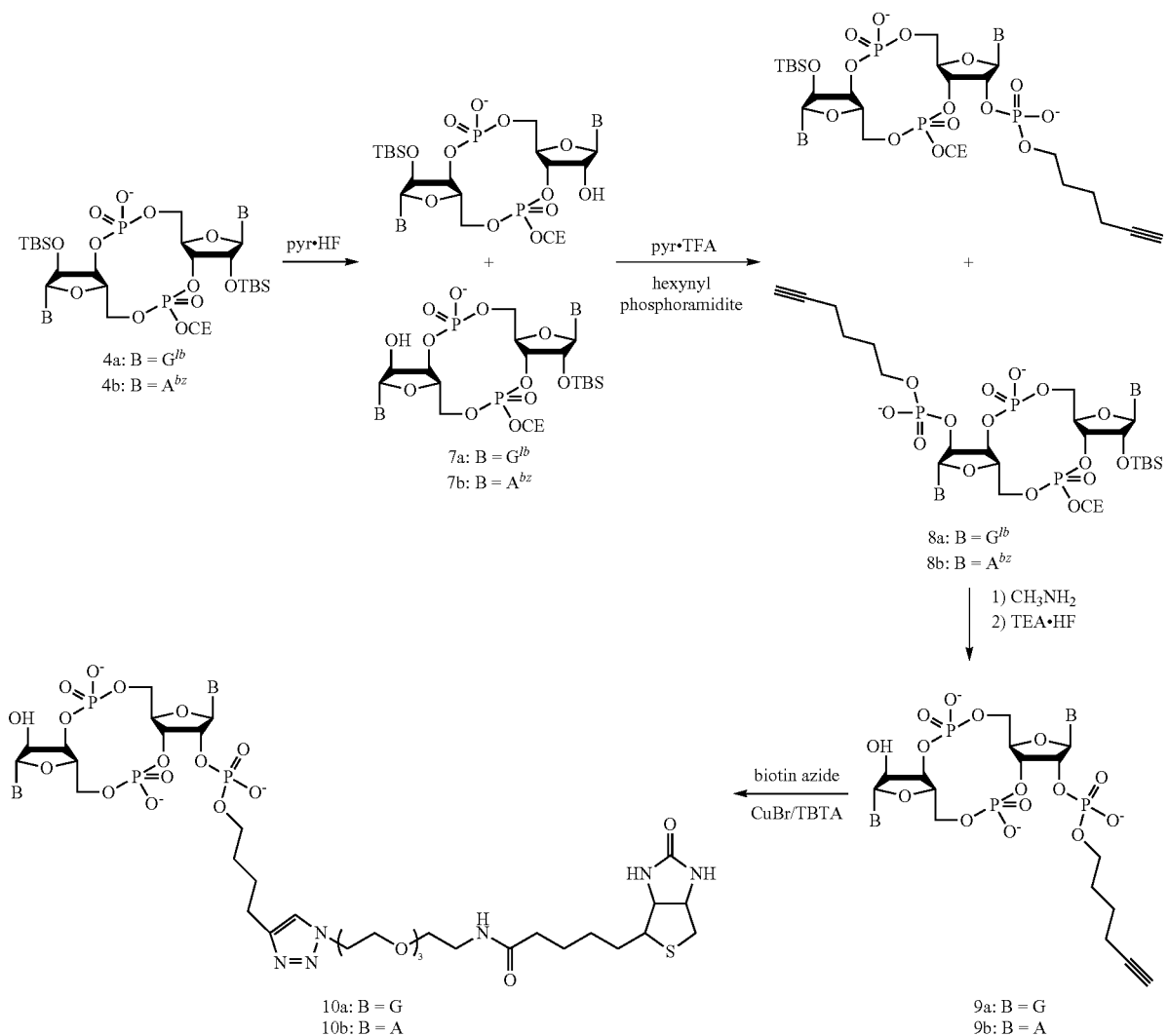

SCHEME 2 Syntheses of biotinylated c-di-GMP and c-di-AMP.

ABBREVIATIONS bz: benzoyl; c-di-AMP: cyclic diadenosine monophosphate; c-di-GMP: cyclic diguanosine monophosphate; DCA dichloroacetic acid; DMOCP: 5,5-dimethyl-2-oxo-2-chloro-1,3,2-dioxaphosphinane; DMSO: dimethylsulfoxide; ib: isobutyryl; RBF: round bottom flask; RP HPLC: reverse phase high pressure liquid chromatography; TBS: tert-butyldimethylsilyl; TBTA: tris((1-benzyl-1H-1,2,3-triazol-4-yl)methyl)amine; TEAA: triethylammonium acetate.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A compound of formula I or formula II:

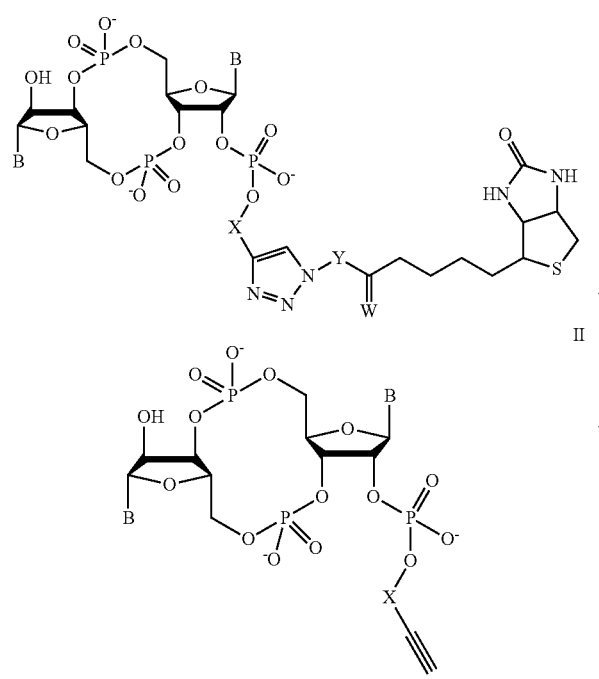

wherein:
each B is independently

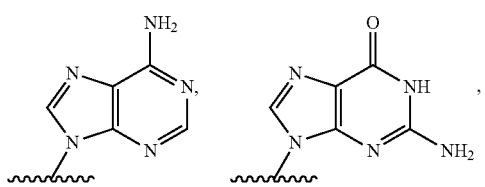

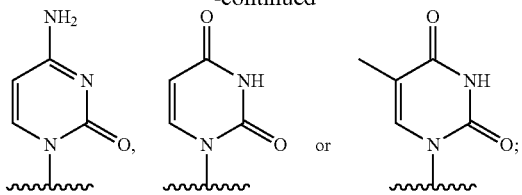

X is $(C_2-C_8)$alkyl, $(C_2-C_8)$alkenyl or $(C_2-C_8)$alkynyl, wherein one or more carbon atoms of the $(C_2-C_8)$alkyl, $(C_2-C_8)$alkenyl or $(C_2-C_8)$alkynyl may be optionally replaced with one or more groups independently selected from O, S, C(=O) and $NR^a$ provided that the O, S or $NR^a$ are not adjacent to any other O, S or $NR^a$, and wherein any $(C_2-C_8)$alkyl, $(C_2-C_8)$alkenyl or $(C_2-C_8)$ alkynyl of X is optionally substituted with one or more groups independently selected from halogen, $OR^b$ and $NR^b{}_2$;

Y is $(C_2-C_{28})$alkyl, $(C_2-C_{28})$alkenyl or $(C_2-C_{28})$alkynyl, wherein one or more carbon atoms of the $(C_2-C_{28})$alkyl, $(C_2-C_{28})$alkenyl or $(C_2-C_{28})$alkynyl may be optionally replaced with one or more groups independently selected from O, S, C(=O) and $NR^c$ provided that the O, S or $NR^c$ are not adjacent to any other O, S or $NR^c$, and wherein any $(C_2-C_{28})$alkyl, $(C_2-C_{28})$alkenyl or $(C_2-C_{28})$ alkynyl of Y is optionally substituted with one or more groups independently selected from halogen, $OR^d$ and $NR^d{}_2$;

W is O or S;

each $R^a$ is independently selected from H and $(C_1-C_6)$alkyl;

each $R^b$ is independently selected from H and $(C_1-C_6)$alkyl;

each $R^c$ is independently selected from H and $(C_1-C_6)$alkyl; and each $R^d$ is independently selected from H and $(C_1-C_6)$alkyl;

or a salt thereof.

2. The compound of claim 1, which is a compound of formula I:

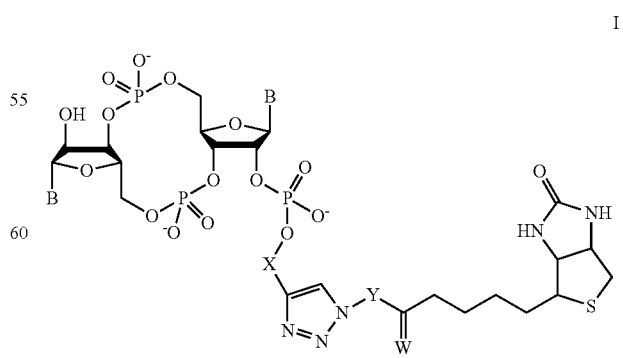

or a salt thereof.

3. The compound of claim 1, which is a compound of formula II:

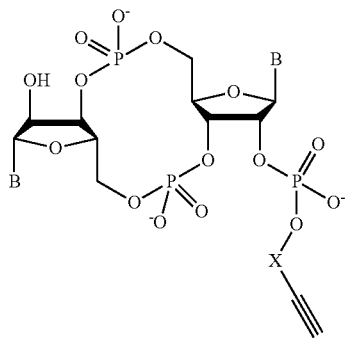

or a salt thereof.

4. The compound of claim 1, which is a compound of formula Ia:

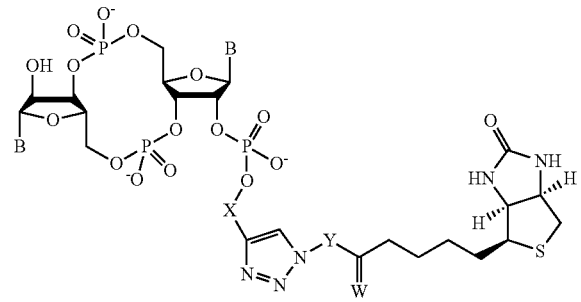

or a salt thereof.

5. The compound of claim 1, wherein each B is:

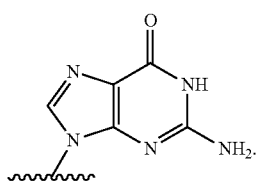 [SMILES: *n1cnc2c(=O)[nH]c(N)nc21]

6. The compound of claim 1, wherein each B is:

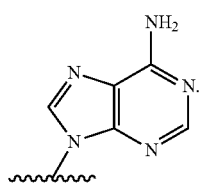 [SMILES: *n1cnc2c(N)ncnc21]

7. The compound of claim 1, wherein W is O.

8. The compound of claim 1, wherein X is $(C_3-C_8)$alkyl, $(C_2-C_8)$alkenyl or $(C_2-C_8)$alkynyl, wherein one or more carbon atoms of the $(C_3-C_8)$alkyl, $(C_2-C_8)$alkenyl or $(C_2-C_8)$alkynyl may be optionally replaced with one or more groups independently selected from O, S, C(=O) and $NR^a$ provided that the O, S or $NR^a$ are not adjacent to any other O, S or $NR^a$, and wherein any $(C_3-C_8)$alkyl, $(C_2-C_8)$alkenyl or $(C_2-C_8)$alkynyl of X is optionally substituted with one or more groups independently selected from halogen, $OR^b$ and $NR^b{}_2$.

9. The compound of claim 1, wherein X is $(C_3-C_8)$alkyl, wherein one or more carbon atoms of the $(C_3-C_8)$alkyl may be optionally replaced with one or more groups independently selected from O, S, C(=O) and $NR^a$ provided that the O, S or $NR^a$ are not adjacent to any other O, S or $NR^a$.

10. The compound of claim 1, wherein X is $(C_2-C_8)$alkyl, $(C_2-C_8)$alkenyl or $(C_2-C_8)$alkynyl.

11. The compound of claim 1, wherein X is $-(CH_2)_4-$.

12. The compound of claim 1, wherein Y is $(C_2-C_{28})$alkyl, $(C_2-C_{28})$alkenyl or $(C_2-C_{28})$alkynyl, wherein one or more carbon atoms of the $(C_2-C_{28})$alkyl, $(C_2-C_{28})$alkenyl or $(C_2-C_{28})$alkynyl may be optionally replaced with one or more groups independently selected from O, S, C(=O) and $NR^c$ provided that the O, S or $NR^c$ are not adjacent to any other O, S or $NR^c$.

13. The compound of claim 1, wherein Y is $(C_2-C_{28})$alkyl, wherein one or more carbon atoms of the $(C_2-C_{28})$alkyl may be optionally replaced with one or more groups independently selected from O, C(=O) and $NR^c$ provided that the O or $NR^c$ are not adjacent to any other O or $NR^c$.

14. The compound of claim 1, wherein Y is $(C_2-C_{28})$alkyl, wherein one or more carbon atoms of the $(C_2-C_{28})$alkyl may be optionally replaced with 1-5 groups independently selected from O and $NR^c$ provided that the O or $NR^c$ are not adjacent to any other O or $NR^c$.

15. The compound of claim 1, wherein Y is:

wherein n is 0, 1, 2, 3 or 4;
each $Y^1$ is independently $(C_2-C_4)$alkyl;
$Y^2$ is $(C_2-C_6)$alkyl;
$Y^3$ is $-NR^{Y4}-$, $-O-$ or $-S-$; and
$R^{Y4}$ is H or $(C_1-C_6)$alkyl.

16. The compound of claim 1, wherein Y is:

17. The compound of claim 1, wherein each $R^a$, $R^b$, $R^c$ and $R^d$ is H.

18. The compound of claim 1 which is:
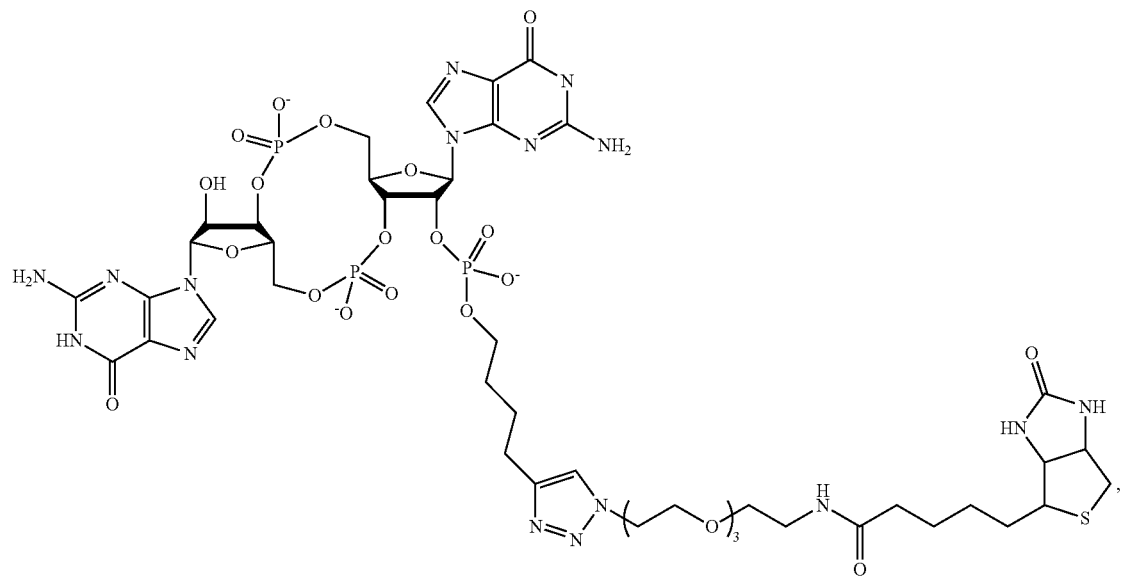
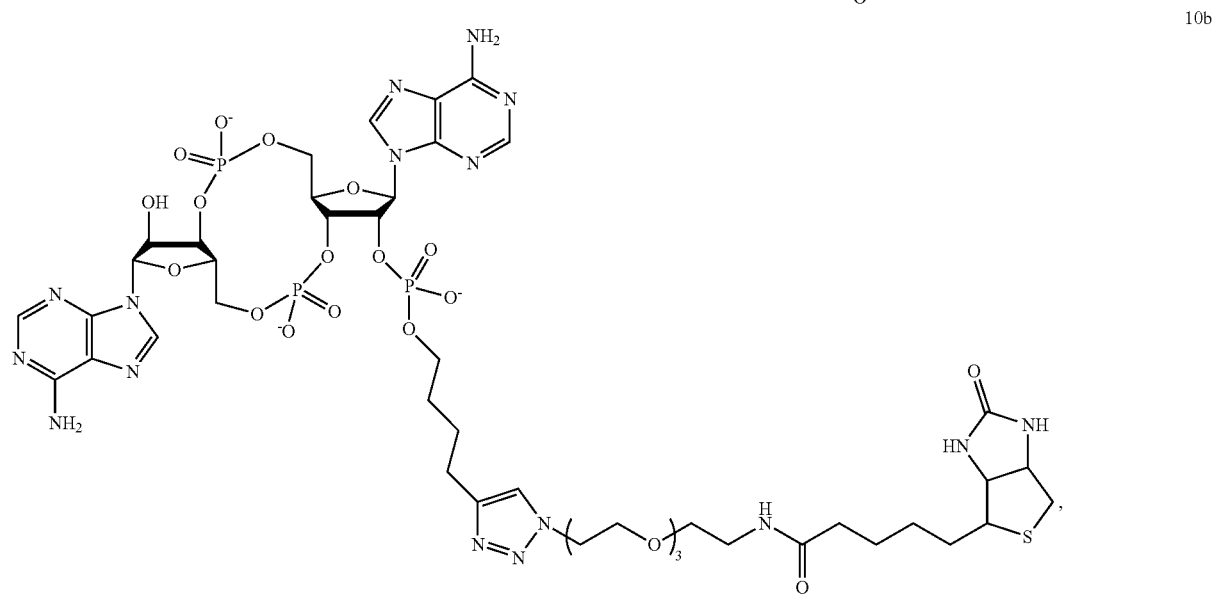
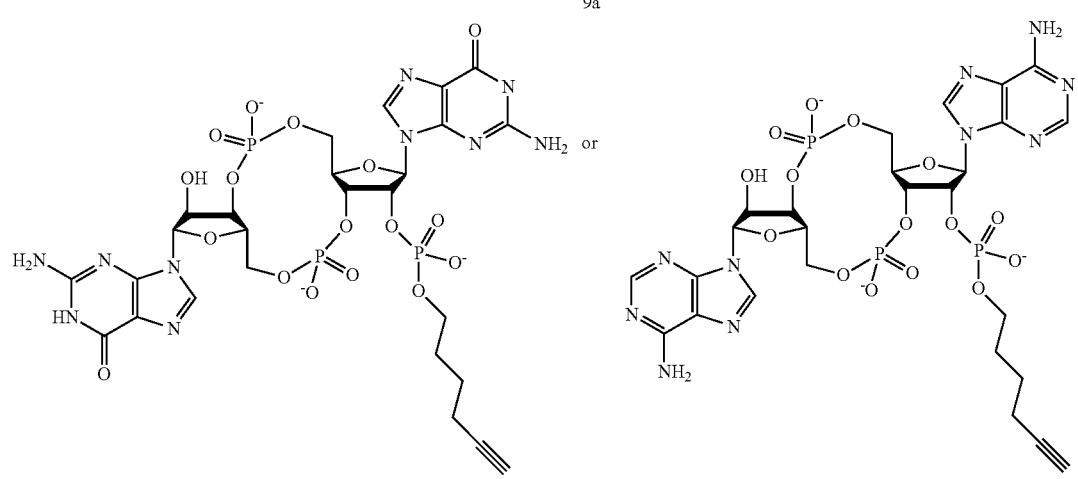
or a salt thereof.

19. The compound of claim 1, or a salt thereof, wherein the salt is a pharmaceutically acceptable salt.

20. A composition comprising a compound of claim 1, or a salt thereof, and an acceptable carrier.

\* \* \* \* \*